United States Patent
Racioppi

(10) Patent No.: US 11,426,389 B2
(45) Date of Patent: Aug. 30, 2022

(54) COMPOSITIONS AND METHODS FOR PROMOTING HEMATOPOIETIC STEM CELL REGENERATION

(71) Applicants: Duke University, Durham, NC (US); Luigi Racioppi, Durham, NC (US)

(72) Inventor: Luigi Racioppi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/634,611

(22) PCT Filed: Jul. 27, 2018

(86) PCT No.: PCT/US2018/044201
§ 371 (c)(1),
(2) Date: Jan. 28, 2020

(87) PCT Pub. No.: WO2019/023650
PCT Pub. Date: Jan. 31, 2019

(65) Prior Publication Data
US 2020/0268722 A1 Aug. 27, 2020

Related U.S. Application Data
(60) Provisional application No. 62/538,027, filed on Jul. 28, 2017.

(51) Int. Cl.
*A61K 31/4748* (2006.01)
*A61K 31/437* (2006.01)
*A61P 7/06* (2006.01)

(52) U.S. Cl.
CPC .............. *A61K 31/437* (2013.01); *A61P 7/06* (2018.01)

(58) Field of Classification Search
CPC .............. A61K 31/439; A61K 31/4748; C12N 5/0647; A61P 7/00
USPC ....................................................... 514/283
See application file for complete search history.

(56) References Cited

U.S. PATENT DOCUMENTS

| | | | |
|---|---|---|---|
| 6,914,128 | B1 | 7/2005 | Salfeld et al. |
| 9,879,005 | B2 * | 1/2018 | Cousins ............... C07D 471/04 |
| 2012/0214728 | A1 | 8/2012 | Van Zant et al. |
| 2014/0234322 | A1 | 8/2014 | Chen et al. |
| 2015/0174173 | A1 | 6/2015 | Ratajczak et al. |
| 2015/0273055 | A1 | 10/2015 | Smith et al. |
| 2016/0199457 | A1 | 7/2016 | Lewcock et al. |
| 2017/0027928 | A1 | 2/2017 | McDonnell et al. |

FOREIGN PATENT DOCUMENTS

WO 2001/058956 A2 1/2001

OTHER PUBLICATIONS

Accession No. GSE95733 (Feb. 2018).
Barbas et al., "In vitro evolution of a neutralizing human antibody to human immunodeficiency virus type 1 to enhance affinity and broaden strain cross-reactivity," Proc. Nat. Acad. Sci. USA, 1994, 91(9):3809-3813.
Fogarty et al., "Calmodulin-dependent protein kinase kinaseβ activates AMPK without forming a stable complex Synergistic effects of Ca2+ and AMP," Biochem J, 2010, 426(1):109-18.
Hawkins et al., "Selection of phage antibodies by binding affinity. Mimicking affinity maturation," J. Mol. Biol., 1992, 226(3):889-896.
Holt et al., "Domain antibodies: proteins for therapy," Trends in Biotechnology, 2003, 21(11):484-490.
International Search Report and Written Opinion for Application No. PCT/US2018/044201 dated Oct. 16, 2018 (19 pages).
Jackson et al., "In vitro antibody maturation. Improvement of a high affinity, neutralizing antibody against IL-1 beta," J. Immunol., 1995, 154(7):3310-3319.
Lento et al., "Calcium Calmodulin Dependent Kinase Kinase 2 Regulates Hematopoietic Stem Cell Regeneration and Quiescence," Blood, 2014, 124(21):1571.
Marks et al., "By-passing immunization: building high affinity human antibodies by chain shuffling," BioTechnology, 1992, 10(7):779-783.
Monteiro et al., "Activation of the Aryl Hydrocarbon Receptor by the Calcium/Calmodulin-Dependent Protein Kinase Kinase Inhibitor 7-Oxo-7H-benzimidazo[2,1-a]benz[de]isoquinoline-3-carboxylic Acid (STO-609)," Drug Metab Dispos, 2008, 36(12):2556-2563.
Racioppi et al., "Calcium/calmodulin-dependent kinase kinase 2 regulates hematopoietic stem and progenitor cell regeneration," Cell Death Dis, 2017, 8(10):e3076.
Schier et al., "Identification of functional and structural amino-acid residues by parsimonious mutagenesis," Gene, 1995, 169(2):147-155.
Wu et al., "Simultaneous targeting of multiple disease mediators by a dual-variable-domain immunoglobulin," Nature Biotechnology, 2007, 25(11):1290-1297.
Yelton et al., "Affinity maturation of the BR96 anti-carcinoma antibody by codon-based mutagenesis," J. Immunol., 1995, 155(4):1994-2004.

* cited by examiner

Primary Examiner — Charanjit Aulakh
(74) Attorney, Agent, or Firm — Michael Best & Friedrich LLP

(57) ABSTRACT

Described is a method for promoting regeneration of hematopoietic stem and progenitor cells in a subject in need thereof. The method comprises administering to the subject a composition comprising a Ca2+/calmodulin (CaM)-dependent protein kinase kinase 2 (CaMKK2) inhibitor. The CaMKK2 inhibitor may be a small molecule inhibitor, such as 7H-benzimidazo(2,1-a)benz(de)isoquinoline-7-one-3-carboxylic acid (STO-609).

10 Claims, 41 Drawing Sheets

A

Figure 1A:
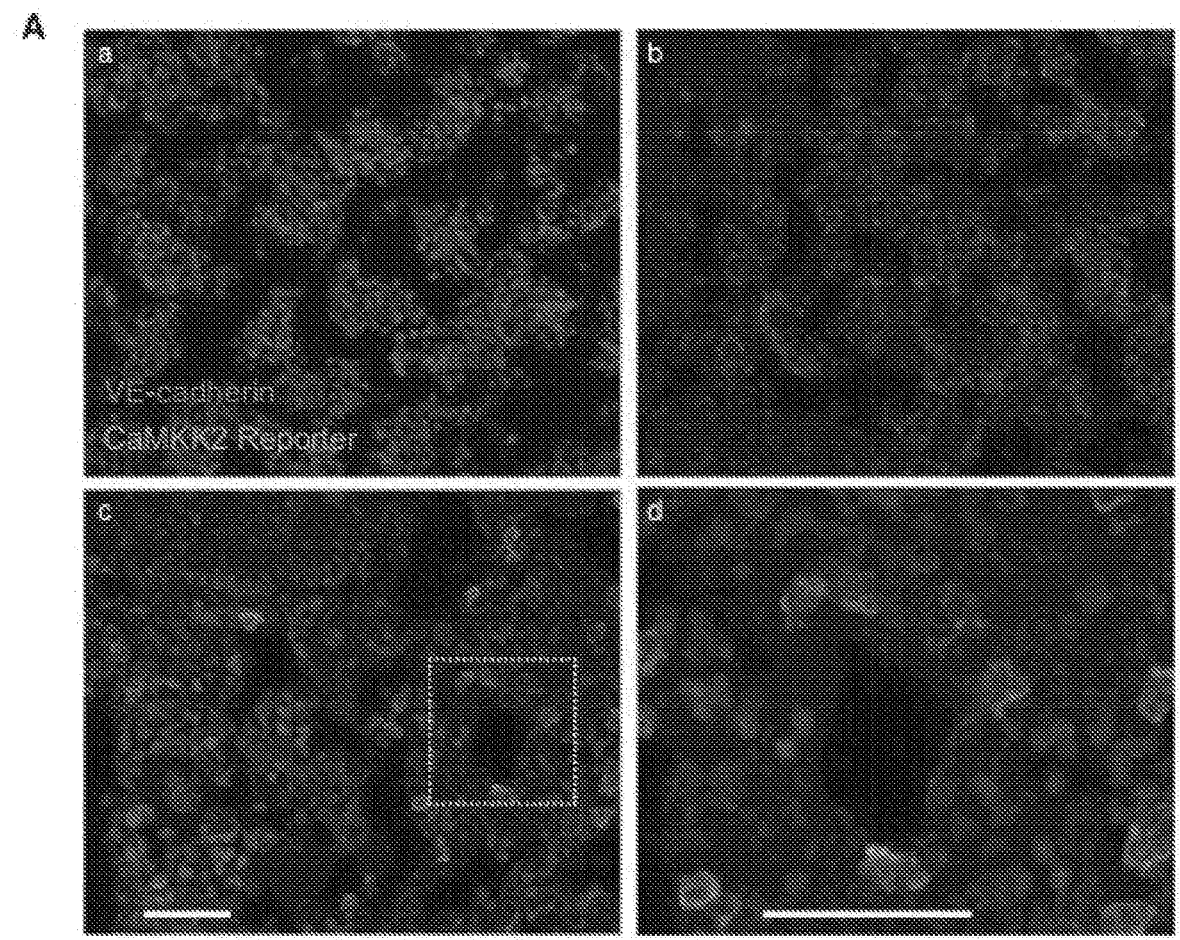

Riddelle et al. Cell 2014   Ng et al. Immunity 2009

A

B

| Signature | Non change[1] | KO DN[2] |
|---|---|---|
| HQ-Sign | 224 | 40 |
| HP-Sign | 308 | 5 |

1, Non significant change in KO compared to WT;
2, Down regualted in KO compared to WT;
P = 0.0001

| Signature | Non change[1] | KO UP[2] |
|---|---|---|
| HQ-Sign | 261 | 3 |
| HP-Sign | 301 | 12 |

1, Non significant change in KO compared to WT;
2, Up regulared in KO compared to WT;
P = 0.0632

FIG. 9B

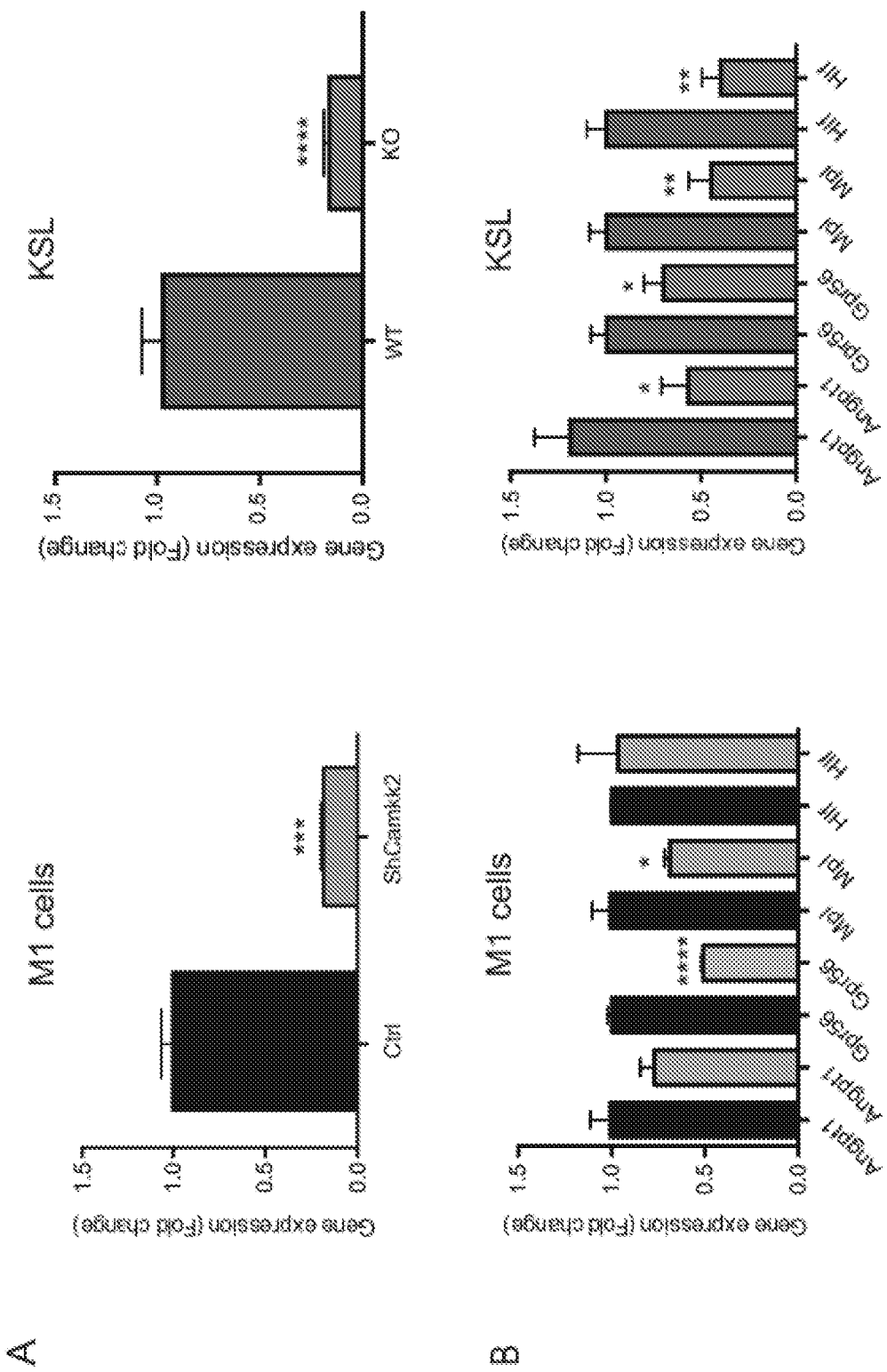
FIG. 15A-B

COMPOSITIONS AND METHODS FOR PROMOTING HEMATOPOIETIC STEM CELL REGENERATION

CROSS REFERENCE TO RELATED APPLICATIONS

This patent application is the U.S. national stage entry, under 35 U.S.C. § 371, of International Application Number PCT/US2018/044201, filed Jul. 27, 2018, which claims priority to U.S. Provisional Application No. 62/538,027, filed Jul. 28, 2017, the entire contents of each of which are hereby incorporated by reference.

STATEMENT OF GOVERNMENT INTEREST

This invention was made with Government support under grant 5U19AI067798-12 and W81XWH-15-1-0443 awarded by the National Institute of Health. The government has certain rights in the invention.

TECHNICAL FIELD

The present disclosure relates to compositions and methods for promoting regeneration of hematopoietic stem and progenitor cells (HSPCs). The compositions and methods may be useful for the treatment of acute hematopoietic radiation syndrome in a subject.

BACKGROUND

Hematopoietic stem and progenitor cells (HSPCs) reside in specialized bone marrow (BM) niches that provide signals to ensure blood production and maintain the long-term hematopoietic stem cell (LT-HSC) pool. Extensive studies of these niches have identified several cell types such as osteoblasts, endothelial cells, osteomacs, regulatory T cells and sympathetic neurons as contributors of the physiologic microenvironment. These cells engage HSPC through both physical contacts and soluble paracrine signaling molecules including CXC chemokine ligand 12 (CXCL12), stem cell factor (SCF), non-canonical and canonical Wnt ligands, and epidermal growth factor to control niche retention and self-renewal. Although these molecules may trigger calcium transients, the role of calcium-dependent cascades in the mechanism regulating HSCP regeneration has not been elucidated. What is needed are methods for promoting regeneration of HSPCs, particularly in subjects in need thereof.

SUMMARY

As described herein, CaMKK2 functions as a critical kinase that regulates the regeneration of HSPCs. CaMKK2 deficiency downregulates genes affiliated with stem cell quiescence and causes a HSPC hyper-proliferative phenotype in vitro and accelerates hematopoietic recovery following radiation injury in vivo. Mechanistically, it is demonstrated that CaMKK2 is required to link radiation injury with AMPK activation and p53 accumulation. Furthermore, the transient inhibition of CaMKK2 with the small molecule CaMKK2 kinase inhibitor STO-609 is shown to improve survival and hematopoietic regeneration.

Disclosed herein is a method for promoting regeneration of HSPCs in a subject in need thereof. The method comprises administering to the subject a composition comprising a CaMKK2 inhibitor. The CaMKK2 inhibitor may be STO-609. The subject may have or be at risk of developing acute hematopoietic radiation syndrome.

Other aspects of the disclosure will become apparent by consideration of the detailed description and accompanying drawings.

BRIEF DESCRIPTIONS OF THE DRAWINGS

Figure 1B:
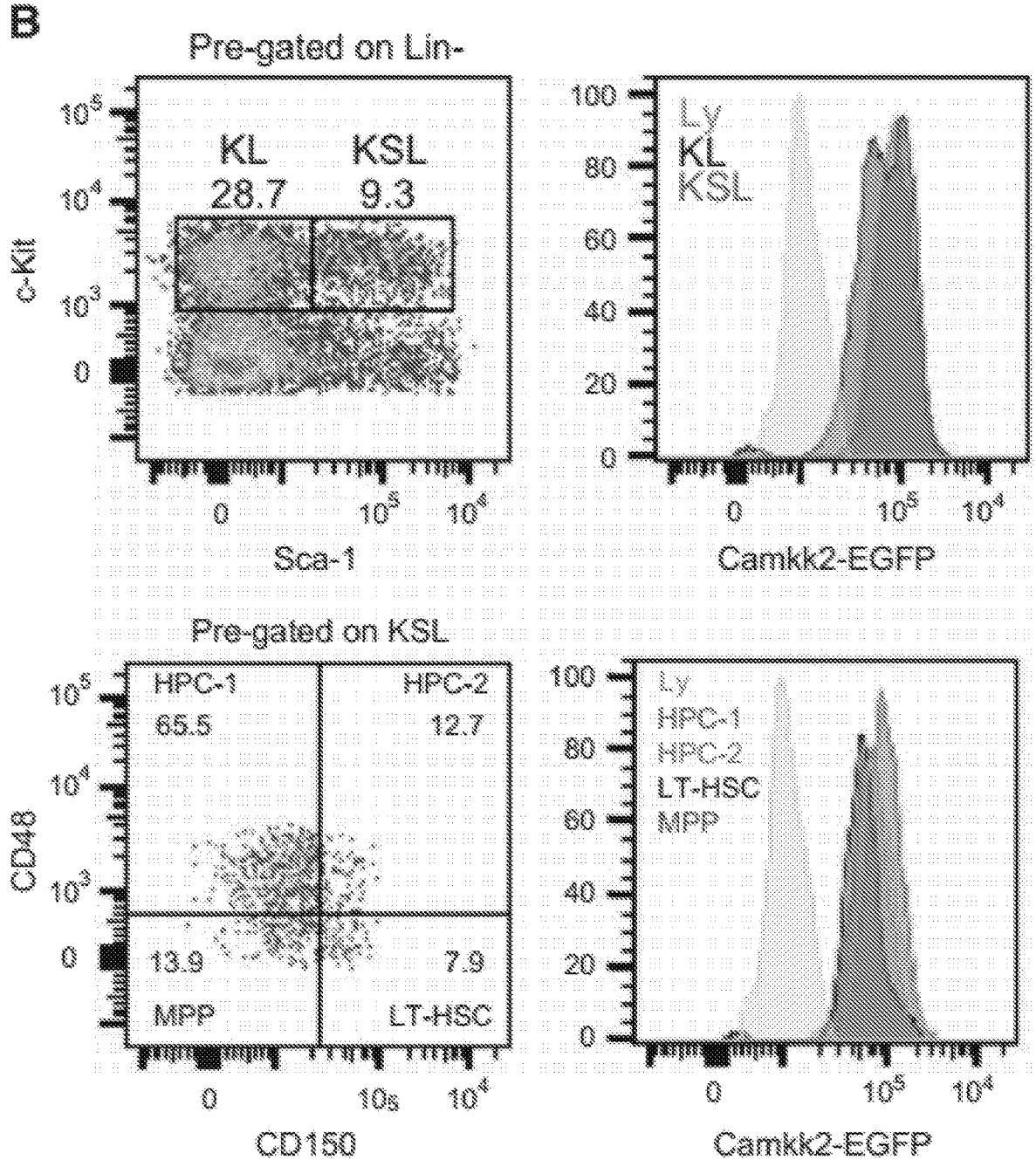
Figure 1C:
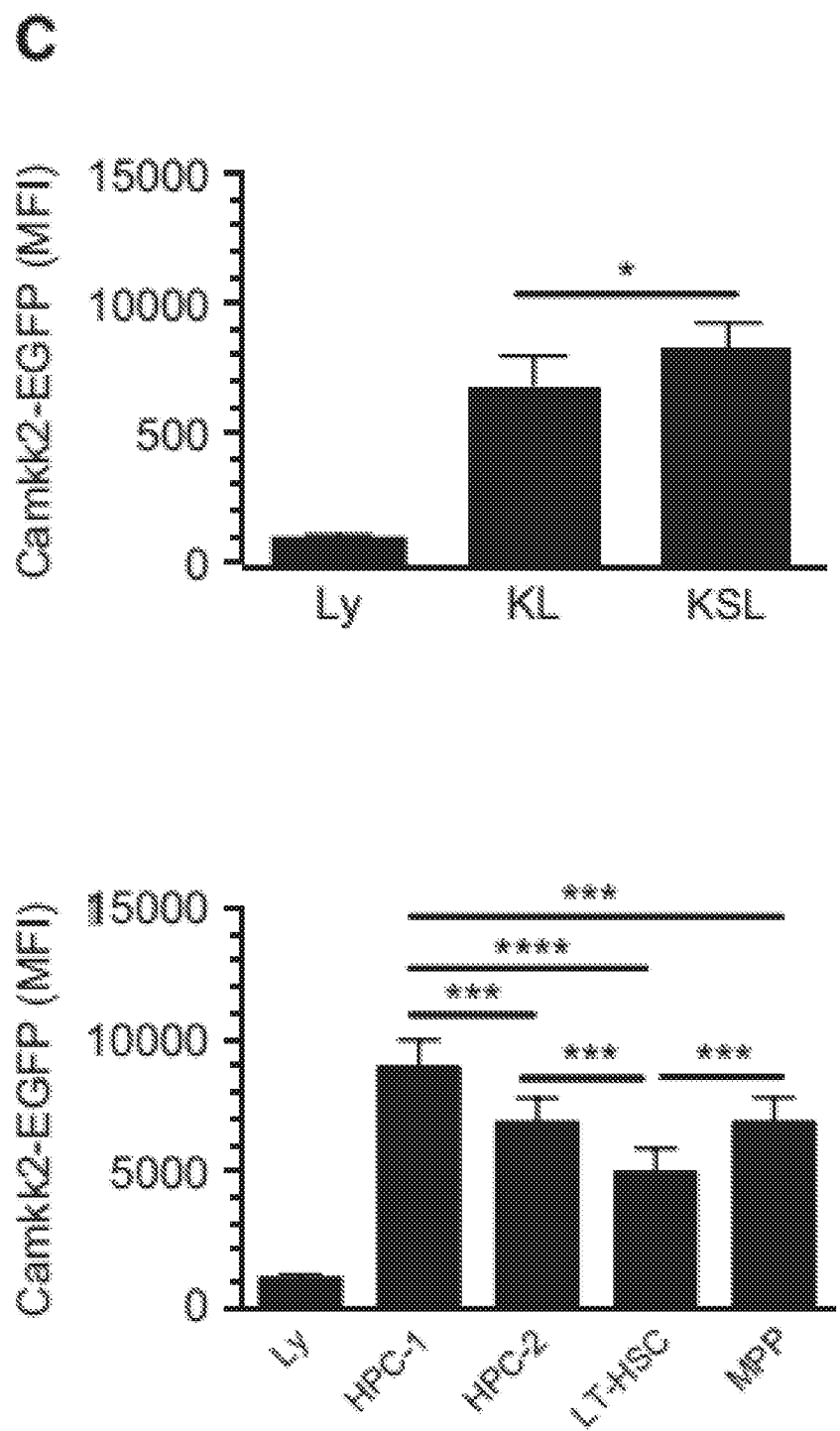

FIGS. 1A-1C. Camkk2 expression is enriched in primitive HSPCs in vivo. (A) Femurs were harvested from control and Camkk2-EGFP reporter mice and sectioned for immunofluorescent staining with VE-cadherin and anti-GFP antibodies (Aa, Ab; low magnification, Ac and insets high magnification) (n=3 per genotype). (B) BM cells from control and Camkk2-EGFP reporter mice were isolated, stained to identify HSPC subsets and analyzed by flow cytometry (top and bottom panels). (C) The reporter expression is shown relative to lymphocyte EGFP intensity, which is considered CaMKK2 negative. The relative EGFP expression is quantitated in the right panels (n=6 mice/genotype). Bars graph reports mean±S.E.M. *, * and ** refer to P-values<0.05, 0.005 and 0.001, respectively FIGS. 2A-2C. Camkk2 regulates transcriptional program of hematopoietic stem cells. (A) Volcano plot comparison of DEGs in KSL cells isolated from BM of Camkk2 null and control mice (WT and KO, respectively). Genes downregulated or upregulated in KO compared with WT are indicated as KO DN and KO UP, respectively. Color dots indicate genes involved in the regulation of differentiation or reprogramming of mature hematopoietic cells to HSC. (B) GSEA of microarray data shows that gene signatures for genes enriched in hematopoietic stem cells are significantly downregulated in KO KSL (upper). In contrast, genes enriched in late progenitors are significantly upregulated in KO KSL (lower). (C) Loss of Camkk2 downregulates the quiescent gene signature in stem cells. Heatmap represents DEGs in quiescent stem cell signature. Q-Sign DN and UP indicate genes downregulated and upregulated in quiescent stem cells. The color key of heatmaps indicates row-wise scaled RPKM values (z-score)

FIGS. 3A-3D. Camkk2 null hematopoietic stem cells have increased proliferation in vitro. KSL cells were sorted from WT and Camkk2 null mice and cultured with TPO, SCF and Flt-3L in the presence or absence of BM endothelial cells (TSF and ECs, respectively). Cell were harvested and analyzed on day 7. (A) Total cells number. (B,C) Absolute numbers of KL and KSL cells. (D) Cells recovered at day 7 were plated in methylcellulose media for colony formation and colonies (CFUs). Graphs report total CFUs normalized by total cell expansion. The experiment was replicated twice. Bars graph reports mean±S.E.M. *P<0.05, P<0.01, *P<0.005. ****P<0.001.

FIGS. 4A-4E. Camkk2 null mice have improved survival and accelerated hematopoietic recovery following TBI. (A) Scheme of TBI. Mice were TBI and monitored for survival, blood cell count (CBC) and BM recovery. (B) Survival of WT and Camkk2 null mice (WT and KO, respectively) irradiated with 800 cGy (n=14 mice per genotype). The blue lines indicate control and the red lines indicate Camkk2 null mice. (C) Hematopoietic recovery in WT and KO mice sublethally irradiated with 700 cGy TBI and bled for CBC analysis of total WBCs, platelets (PLT), RBCs, neutrophils (NE), monocytes (Mo) and lymphocytes (Ly) (n=6 and 9 mice for WT and Camkk2 null mice, respectively). (D) WT and KO mice (n=10 per group) were irradiated with 700 cGy TBI and euthanized 14 days after irradiation. WT and KO non-irradiated mice were used as controls (n=6 mice per group). Upper and lower bar graphs report mean±S.E.M. of KL and KSL, respectively. (E) BrdU incorporation in KL and KSL cells in vivo during regeneration. WT and KO mice were irradiated with 700 cGy TBI, and after 14 days were pulsed with BrdU in vivo for 2 h before killing. Dot plots of KL and KSL cells and BrdU incorporation on day 14 after radiation (top panels). BrdU staining FACS profiles in KL and KSL subsets (upper panels). Bars graph reports mean±S.E.M. The percentage of BrdU+ cells is shown in lower graphs (bottom panels; n=6 per genotype). *P<0.05, P<0.01, *P<0.005, ****P<0.001

Figure 5A:
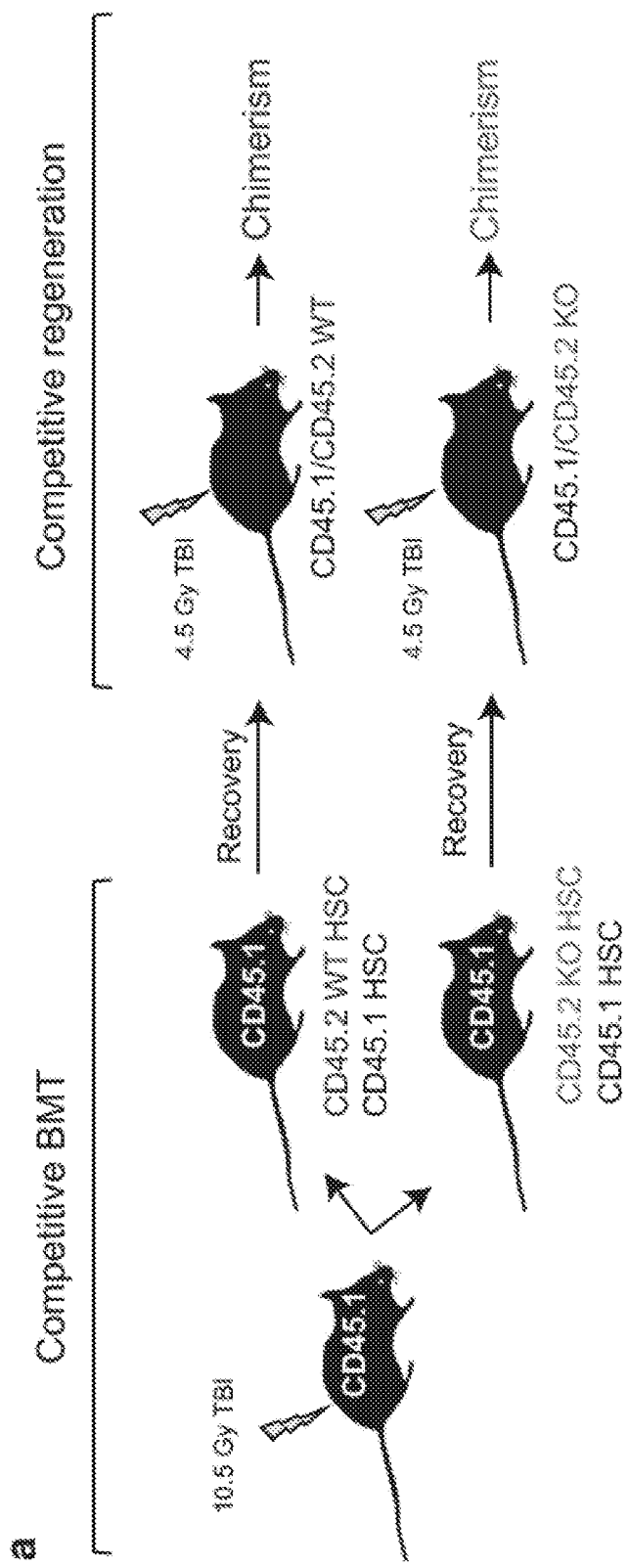
Figures 5B, 5C:
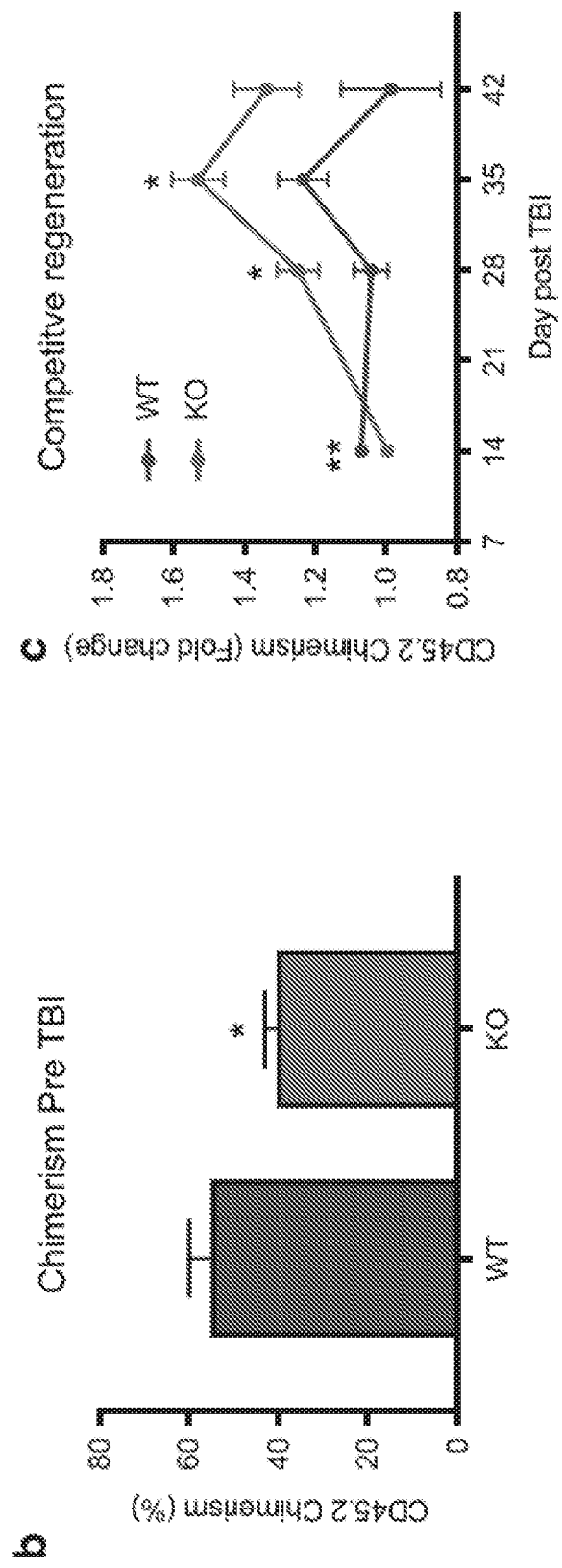

FIGS. 5A-5C. Camkk2 null HSC have a cell-intrinsic enhanced regenerative capability in vivo. KSL CD34⁻ cells were isolated from WT and Camkk2 null mice (WT and KO, respectively) and transplanted in lethally irradiated recipient mice with CD45.1 competitor BM. The recipient mice receiving WT or KO KSL CD34⁻ cells were monitored for 4 months. Subsequently, mice showing comparable percentages of WT or KO donor CD45.2 cells were irradiated with 450 cGy TBI and bled weekly after irradiation (n=6 per group). (A) Scheme of the experiment. (B) CD45.2 chimerism in mice reconstituted with WT or KO KSL CD34⁻ before receiving 4.5 Gy TBI. (C) Donor CD45.2 chimerism was monitored by flow cytometry and the results are expressed as fold change over the basal level (pre-TBI). Bars graph reports mean±S.E.M. *P<0.05, **P<0.

FIG. 6A-6F. CaMKK2 couples radiation signaling with the AMPK anti-proliferative pathway. HSPC (KL+KSL) were isolated from WT and Camkk2 null (KO) mice and irradiated in vitro with 400 cGy or left non-irradiated. Cells were then cultured for 1-h in regular medium. Protein expression was normalized by actin and expressed as fold change over basal (non-irradiated WT HSPC), and is reported on the top of each lane. (A) Immunoblots of CaMKK2, phospho-CaMK1 (pCaMK1) and actin. (B) Immunoblots of Tp53, phosphorylated AMPK and S6rp (pAMPK and pS6rp, respectively). (C-E) M1 myeloid progenitor cells were transduced with lentiviral vectors expressing a short hairpin sequence for silencing Camkk2 or a control sequence (ShCamkk2 and Ctrl, respectively). Ctrl and ShCamkk2 M1 cells were then irradiated or left non-irradiated. One-hour after irradiation, M1 cell protein expression was assessed by immunoblotting. (C) Expression of CaMKK2 and actin. (D) Immunoblots of pAMPK, pS6rp, actin and Tp53 of M1 cells irradiated with increasing doses of radiation or left non-irradiated. (E) M1 cells transduced with Ctrl and ShCamkk2 lentiviral vectors were 300 cGy irradiated and cultured for 24 h in regular medium in the presence or absence of AICAR (100 µM), a cell permeable AMPK agonist (Top and lower, respectively). Cell number was determined using a colorimetric assay, and the results are expressed as fold change of non-irradiated cells cultured in the absence of AICAR. Bars graph reports mean±S.E.M. The experiments included in this figures were replicated at least three times. (F) Modeling the radiation-induced CaMKK2-dependent signal pathway. P<0.01, *P<0.005, ****P<0.001

FIGS. 7A-7D. Pharmacologic inhibition of CaMKK2 enhances hematopoietic regeneration in vivo. Treatment with STO-609, a CaMKK2 inhibitor, mitigates the acute hematopoietic radiation syndrome. (A) Scheme of irradiation and STO-609 treatment in wild type mice. (B) Survival of 900 cGy TBI wild-type mice treated with vehicle or STO-609 (n=10 per group). Wild-type mice were irradiated with 500 cGy TBI and were then treated with STO-609 or vehicle after 24 h. Nine days after TBI, the mice were killed and bones were removed. The BM cells were counted and stained to identify HSPC (BMC). (C) Representative staining and gating strategy. (D) Absolute number of BMC and HSPC (upper and lower graph, respectively). The results are expressed as the fold changes over the absolute number of cells recovered form vehicle-treated wild type mice, and are normalized for one femur. Two independent experiments have been combined (total number of mice-9 per group). Bars graph reports mean±S.E.M. *P-value<0.05, **P-value<0.01/

Figure 8A:
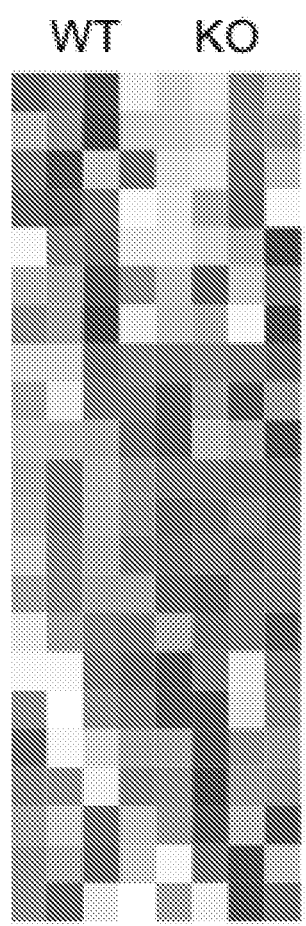
Figure 8A:
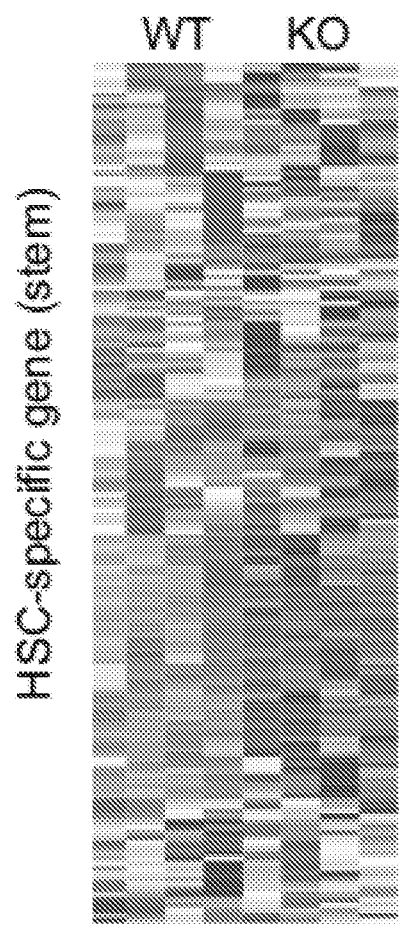
Figure 8B:
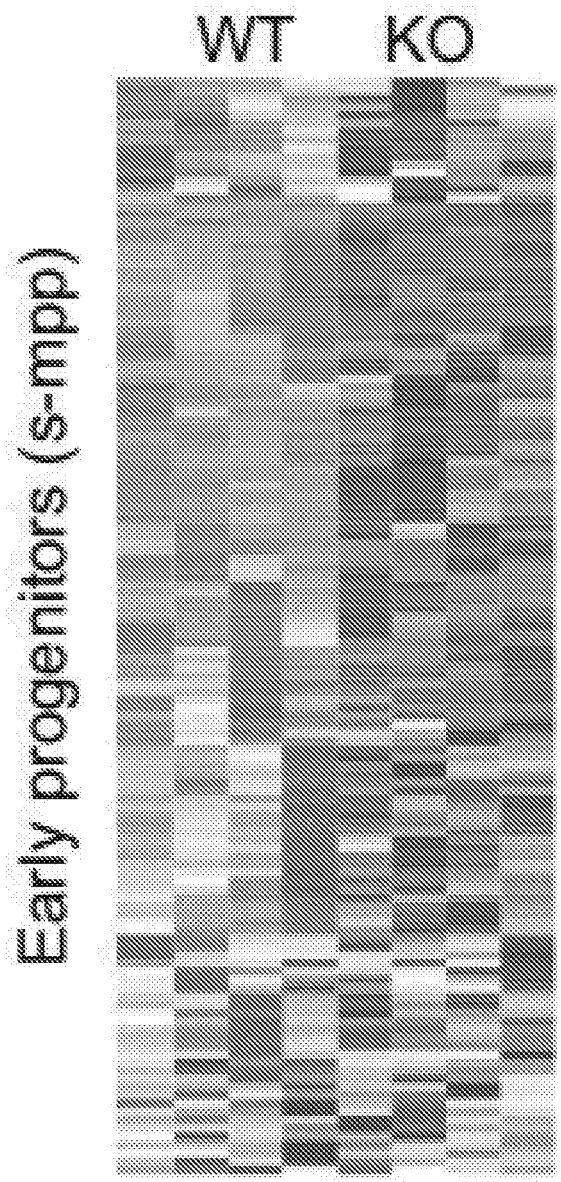
Figure 8C:
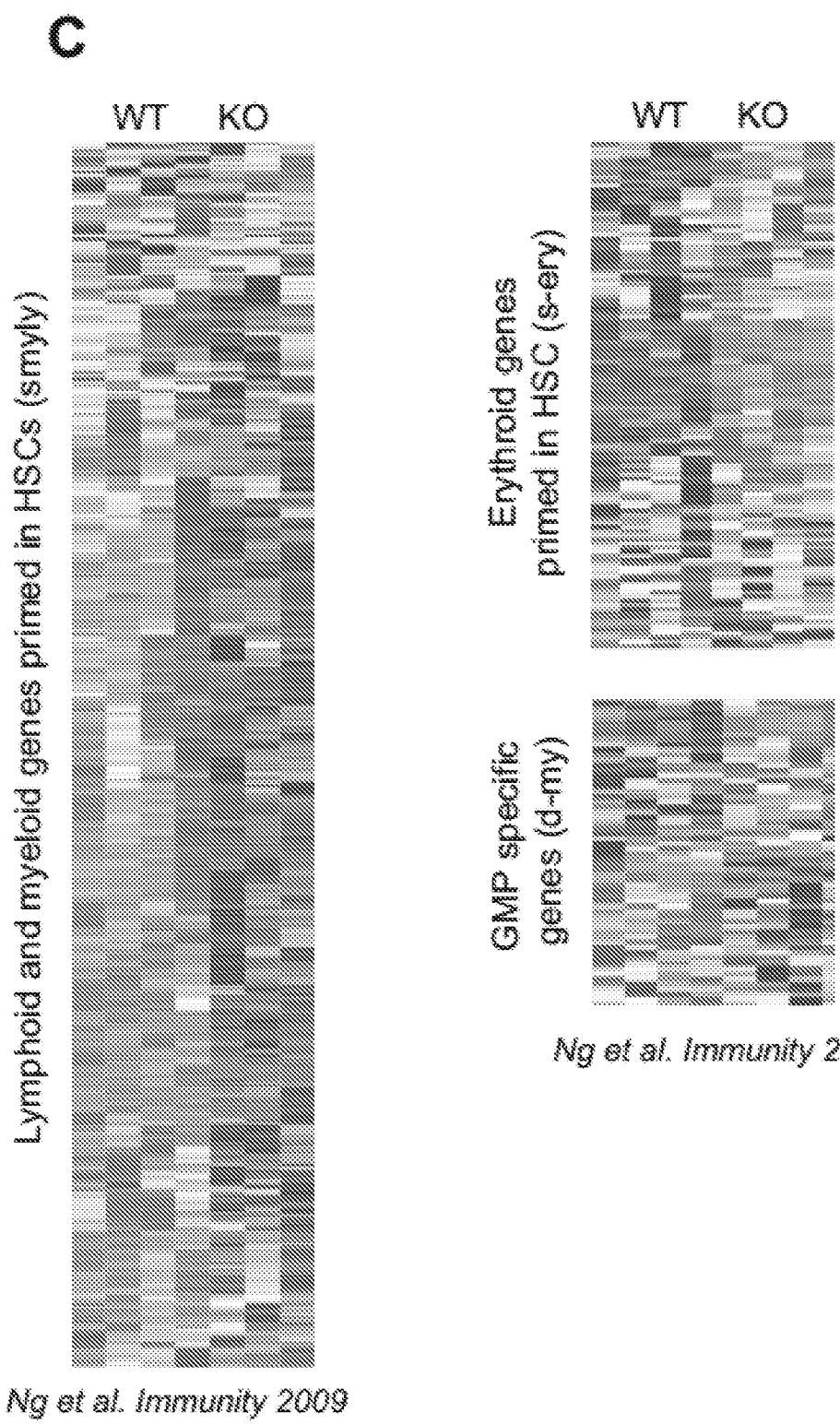

FIGS. 8A-8C. Camkk2 differentially modulate stem cell- and lineageassociated transcriptional programs. Heatmap representation showing differentially expressed genes in: (A) hematopoietic stem cells; (B) immediate downstream progenitors; (C) lineage-affiliated genes in Camkk2 KO compared to WT KSL. Genes in bold red text are reported to induce reprogramming of differentiated hematopoietic cells into induced HSCs. The color key for all heatmaps indicates row-wise scaled RPKM values (z-score).

Figure 9A:
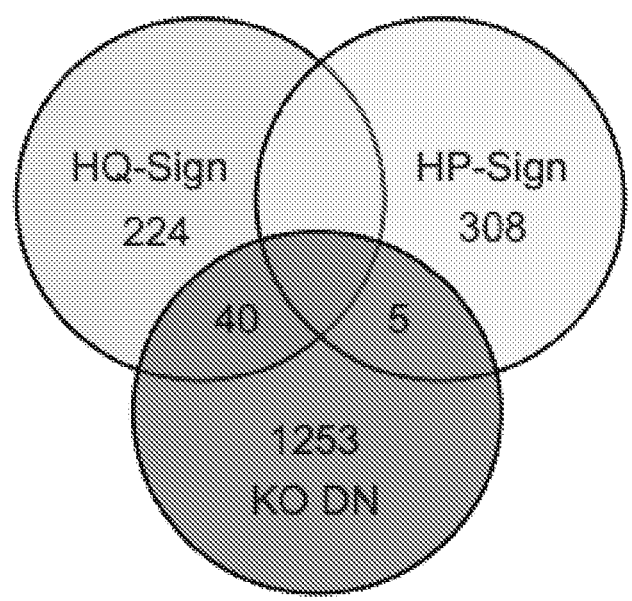
Figure 9A:
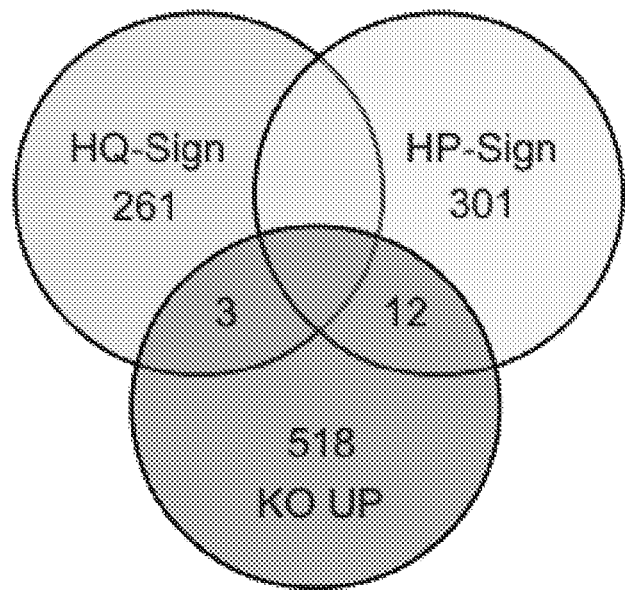
Figure 9C:
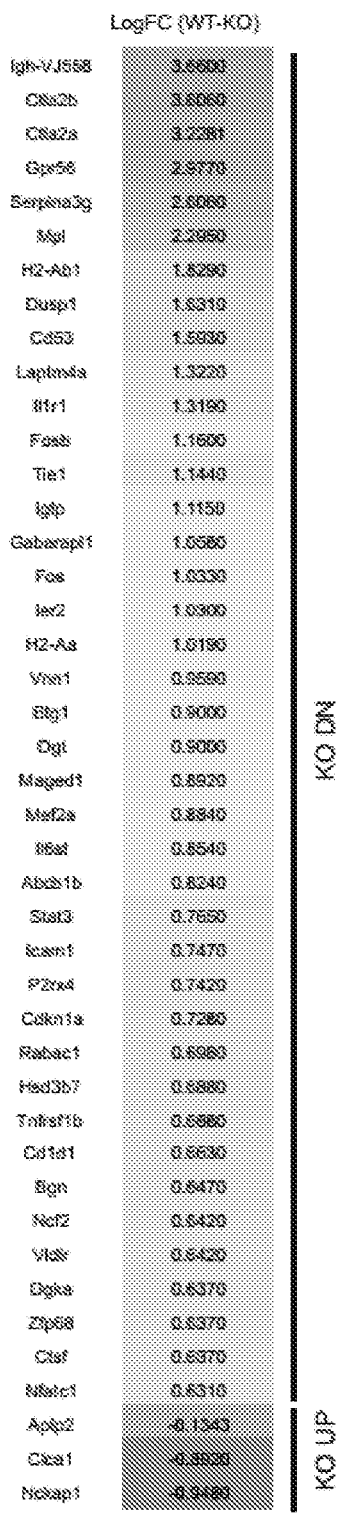

FIGS. 9A-9C. Genes affiliated with hematopoietic stem cell quiescence are down regulated in Camkk2 null KSL. (A) Venn diagram showing the overleaping of genes down or up regulated in Camkk2 null KSL compared to WT (KO DN and KO UP, respectively) with genes affiliated with quiescent or proliferating hematopoietic stem cells (HQ-Sign and HP-Sign, respectively). (B) Genes affiliated with hematopoietic stem cell quiescent signature are significantly downregulated in Camkk2 null KSL (p=0.0001). (C) Loss of Camkk2 downregulates the genetic quiescent signature in stem cells. Fold chance of HQ-Sign genes significantly downregulated in Camkk2 null KSL compared to WT genes. Venny $2.0^2$ was used for Venn diagram analyses.

Figure 10A:
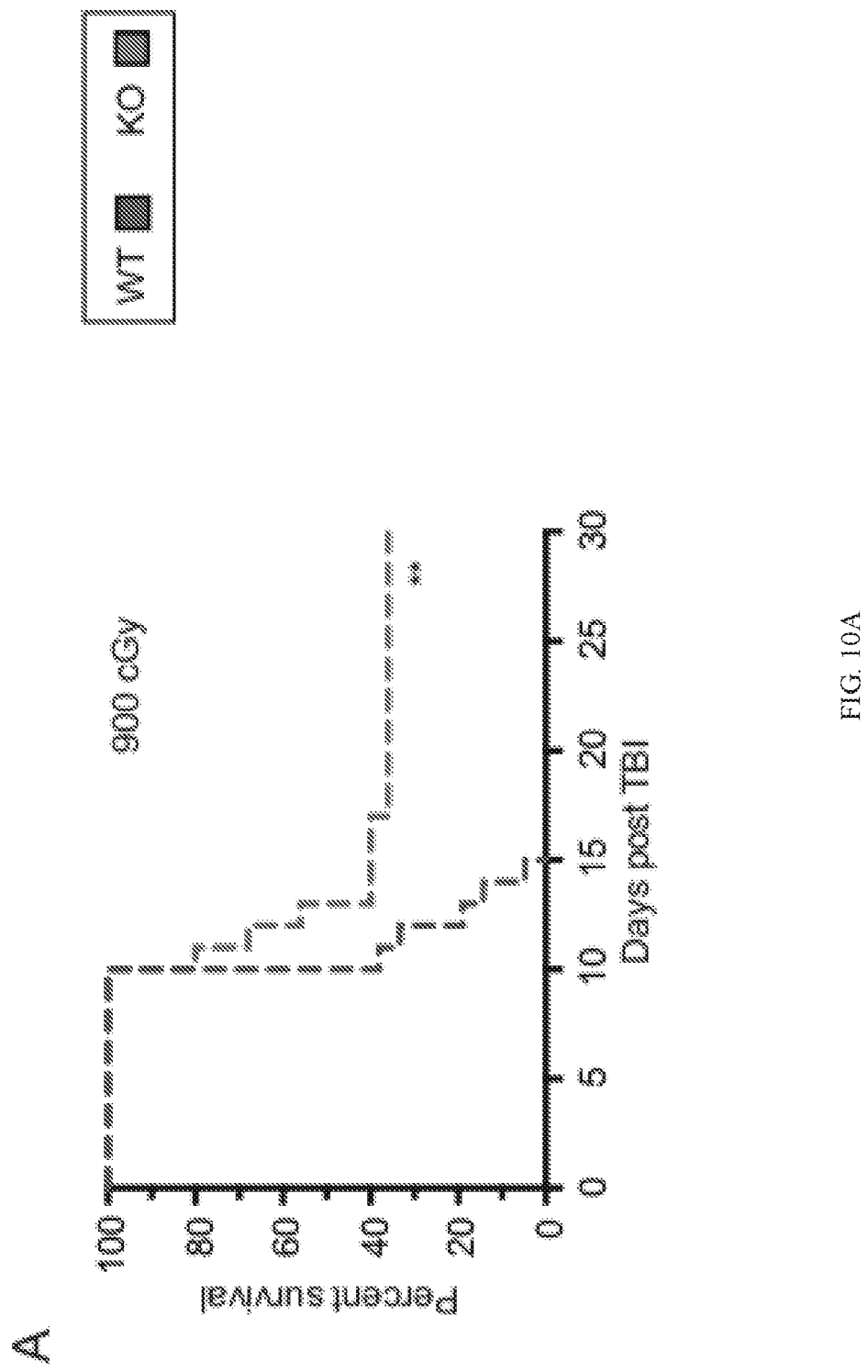
Figure 10B:
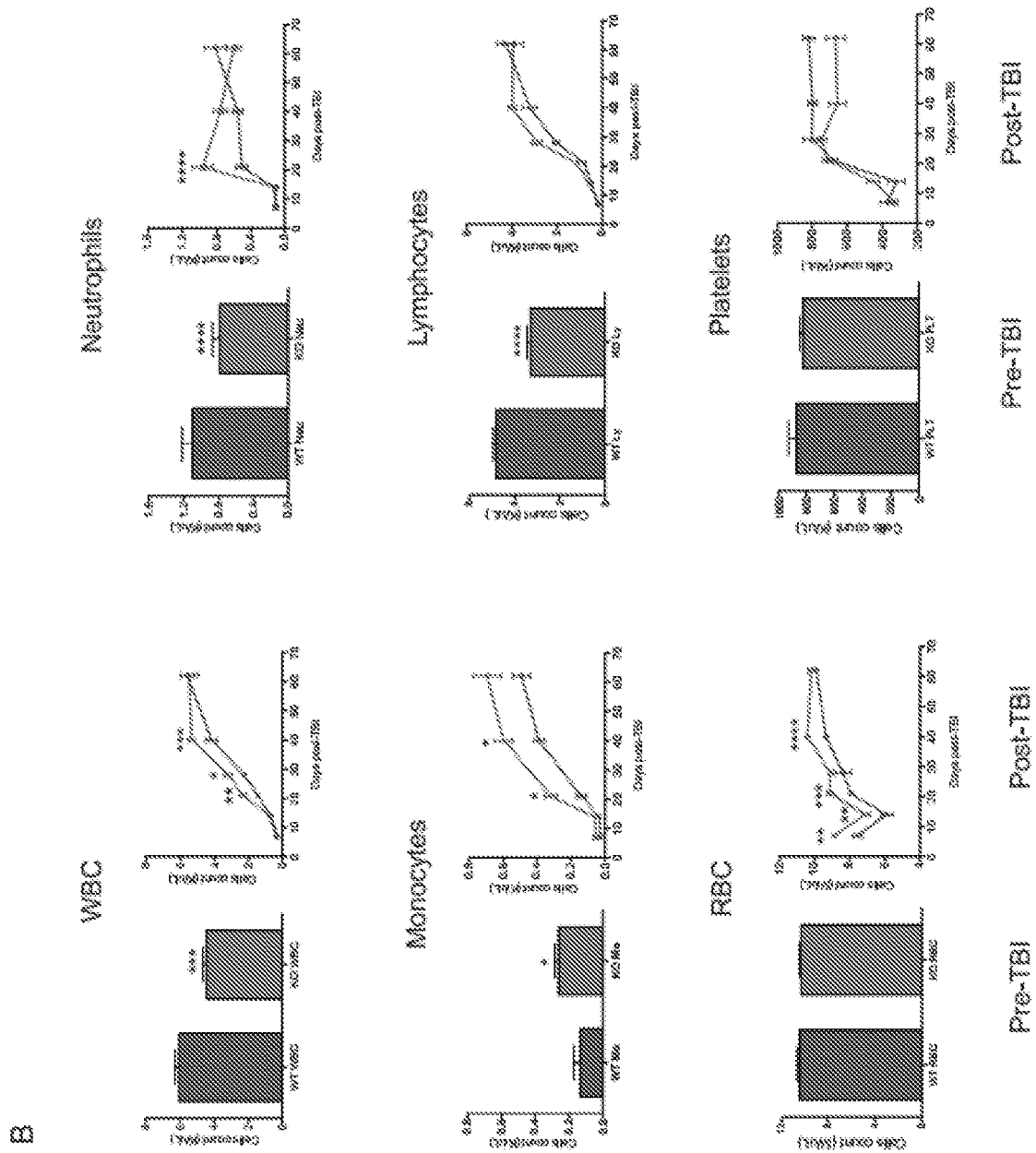

FIGS. 10A-10B. Camkk2 null mice have improved survival and accelerated hematopoietic recovery following total body irradiation. Mice were TBI and monitored for survival and blood cell count recovery. (A) Survival of WT and Camkk2 null mice (WT and KO, respectively) irradiated with 800 cGy (n=13 mice/genotype). (B) Cell blood count number in WT and KO mice TBI with 700 cGy and monitored by CBC (n=6 and 9 for WT and KO group, respectively). The absolute numbers+/−SEM are shown. Bars graphs show pre-TBI CBC. *p<0.05, p<0.01, *p<0.005. ****p<0.001.

FIGS. 11A-11E. Camkk2 null mice have an accelerated bone marrow recovery following total body irradiation. WT and KO mice were irradiated with 700 cGy TBI and sacrificed on day 14. (A) Representative hematoxylin and eosin staining of WT and Camkk2 null mice (WT and KO, respectively) femur sections. (B) Absolute count number of white BM cells (WBMC) isolated from femurs of non-irradiated and TBI mice (left and right bar graphs, respectively; n=10 mice/group). Data refers to cells recovered from one bone. (C) Gating strategy to identify SLAM KSL cells. Percentage of SLAM KSL in non-irradiated and TBI WT and KO mice (D and E panels, respectively; n=6 mice/genotype). Bars graph reports mean+/−SEM. *p-values<0.05; **p-values<0.01.

FIGS. 12A-12D. Effect of genetic ablation of Camkk2 on HSPC survival under homeostatic conditions and following total body irradiation. (A) gating strategy to identify KL and KSL live and death cells by using Annexin-V and 7AAD in bone marrow of non-irradiated WT and Camkk2 null mice (WT and KO, respectively). (B) Percentages of live KSL and KL cells in non-irradiated WT and Camkk2 null mice (n=6 mice/genotype). (C) WT and KO mice were euthanized 24-hours after 450 cGy TBI and apoptotic and live KL and KSL cells were identified by flow cytometry. (D) The percentage of Annexin V-/7AAD- live cells in irradiated WT and KO mice is shown (n=6/genotype). Bars graph reports mean+/−SEM. *p-values<0.05.

Figure 13A:
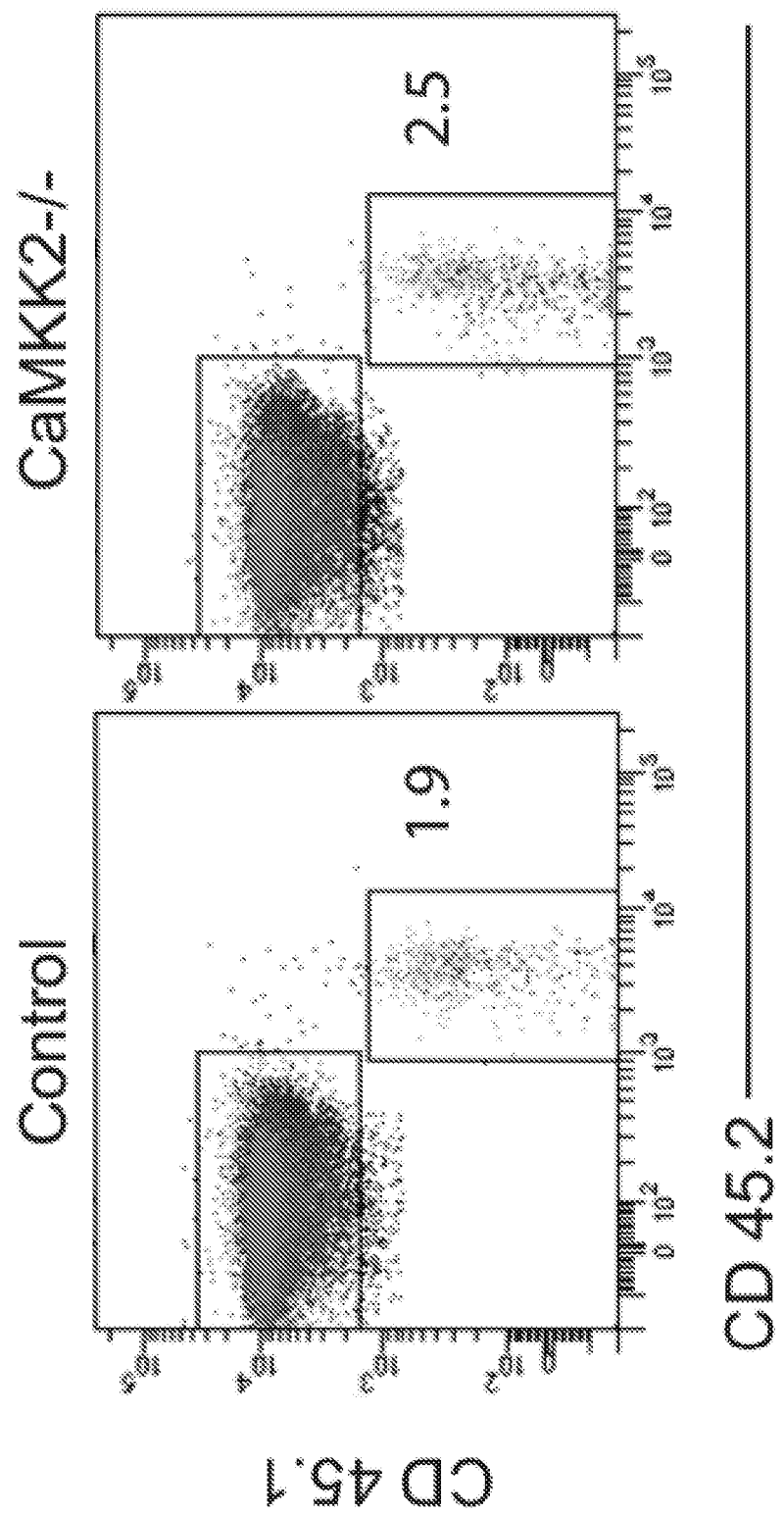
Figure 13B:
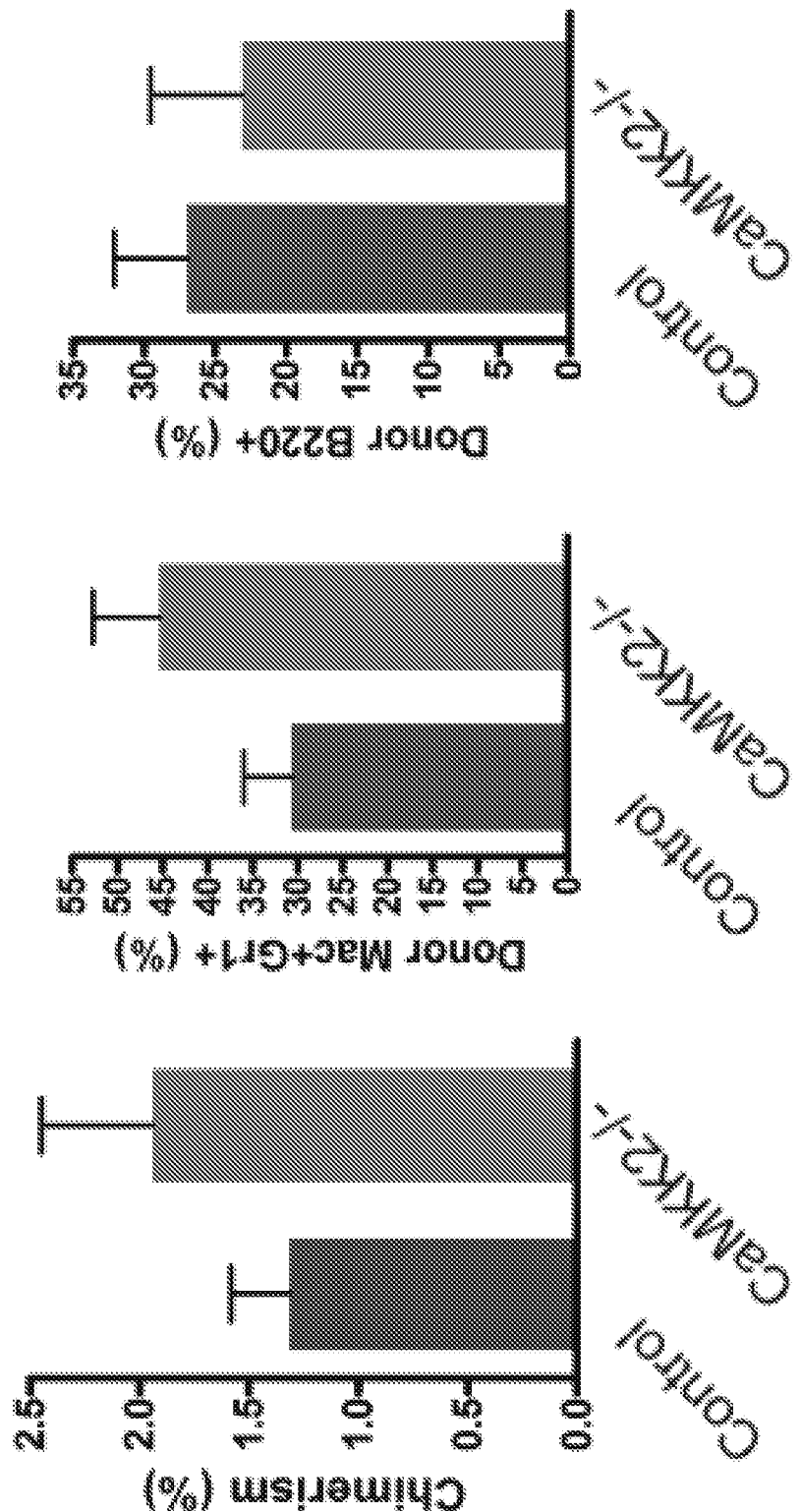

FIGS. 13A-13B. Loss of Camkk2 does not impair the engraftment potential of irradiated hematopoietic stem cells. (A) Control and Camkk2 null mice received 200 cGy TBI and were allowed to regenerate. KSLCD34− cells were then sorted from the irradiated donors and transplanted into lethally irradiated recipient mice with competitor bone marrow. The recipient mice were bled at 8 weeks and donor CD45.2 chimerism was analyzed by flow cytometry. There was no significant difference in peripheral blood chimerism at 8 weeks. Data are quantified in FIG. 13B. The data indicate the accelerated regeneration found in irradiated Camkk2 null HSCs is not associated with decreased transplantation function or malignant transformation. Bars graph reports mean+/−SD; n=6 mice/group).

Figure 14:
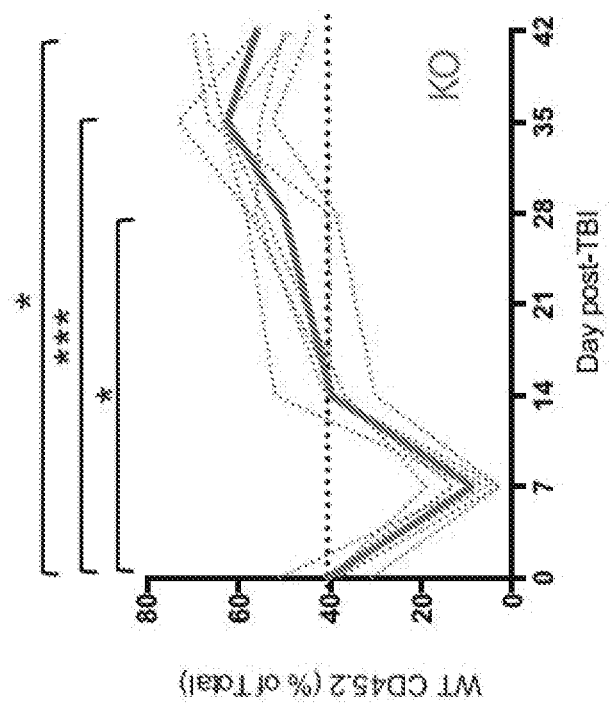
Figure 14:
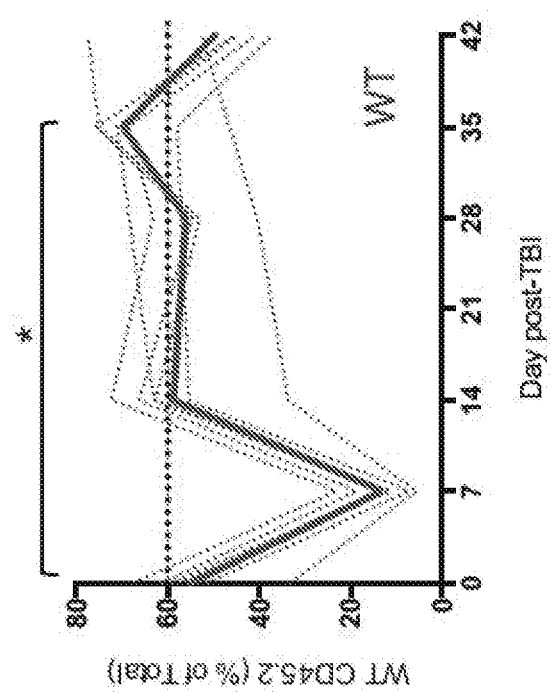

FIG. 14. Camkk2 null HSCs have a cell-intrinsic enhanced regenerative capability in vivo. KSLCD34− cells were isolated from WT and KO and transplanted in lethally irradiated recipient mice with CD45.1 competitor bone marrow. The recipient mice receiving WT or KO KSLCD34− cells were monitored for 4 months. Subsequently, mice showing comparable percentages of WT or KO donor's CD45.2 cells were irradiated with 450 cGy TBI and bled weekly after irradiation. Donor CD45.2 chimerism was monitored by flow cytometry and the results expressed as fold change over the basal level (pre-TBI). Scheme of the experiment and cumulative results have been shown FIG. 5A and FIG. 5B, respectively. FIG. 14 left and right panels show kinetics of CD45.2 chimerism. Blue and red dotted lines indicate % of CD45.2 chimerism in individual mice transplanted with WT (left panel) or KO KSLCD34− cells (right panel), respectively. Blue and red bold lines indicate the average of CD45.2 fold change in WT and KO group, respectively (n=6 mice/group). *p<0.05, p<0.01, *p<0.005

FIGS. 15A-15B. Modeling CaMKK2 deficiency in the myeloblastic M1 cell line. M1 cells were transduced with a lentiviral vector or expressing a control sequence or a short hairpin sequence for silencing Camkk2 (Ctrl and ShCamkk2, respectively). (A) Normalized Camkk2 mRNA expression in M1 cells transduced with control or ShCamkk2 vectors (left; n=6). Camkk2 gene expression in fresh isolated WT and Camkk2 null (KO) KSL (right; n=9). (B) Normalized gene expression in transduced M1 cells and primary WT and KO KSL. The selected genes were highly expressed in both cell types (M1 and KSL), and differentially expressed (DEGs) KO KSL compared to WT. Silencing of Camkk2 in M1 cells and Genetic ablation of CaMKK2 has similar effects on gene expression. Bars graph reports mean+/−SEM. *p<0.05.

DETAILED DESCRIPTION

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity matured antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, *J. Mol. Biol.*, 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11): 1290-1297 (2007) and PCT International Application WO 2001/058956, the contents of each of which are herein incorporated by reference), or domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-GFAP antibody or a GFAP antibody).

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The term "bone marrow injury" as used herein refers to any injury which causes a hematopoietic deficiency in the subject. A "hematopoietic deficiency" refers to a reduction in the amount of one or more hematopoietic cell types, HSCs, and/or HPCs below a normal level. For example, a bone marrow injury may cause depleted stores of HSPCs in the bone marrow. Bone marrow injury may be caused by numerous hematological stressors, including chemotherapy, radiation, blood loss, and infection.

The term "CaMKK2 inhibitor" as used herein refers to any agent that reduces the level and/or activity of CaMKK2.

The terms "compositions", "CaMKK2 inhibitor compositions", or "compositions comprising a CaMKK2 inhibitor" are used interchangeably herein to refer to a composition comprising a CaMKK2 inhibitor. The disclosed compositions may be used in a method of promoting regeneration of HSPCs in a subject in need thereof.

The term "differentiation" as used herein refers to both the change of hematopoietic stem cells into hematopoietic progenitor cells and the change of hematopoietic progenitor cells into mature cells including erythrocytes, leukocytes and megakaryocytes.

The terms "effective amount" or "therapeutically effective amount" as used herein, refers to a dosage of the CaMKK2 compositions effective for eliciting a desired effect. For example, an "effective amount" or the CaMKK2 composition may be the amount effective for promoting regeneration of HSPCs in a subject. As another example, the "effective amount" of the CaMKK2 composition may be the amount effective for treating or preventing acute hematopoietic radiation syndrome in the subject.

The term "hematopoietic cells" as used herein include all types of blood cells from the myeloid (monocyte, macrophases, neutrophils, basophils, eosinophils, erythrocytes, platelets and dendritic cells) and lymphoid lineages (T-cells, B-cells and NK-cells).

The terms "hematopoietic stem cell" or "HSC" as used interchangeably herein refer to multipotent stem cells that are capable of differentiating into all types of blood cells. HSCs are capable of differentiating into all blood cells from the myeloid (monocyte, macrophases, neutrophils, basophils, eosinophils, erythrocytes, platelets and dendritic cells) and lymphoid lineages (T-cells, B-cells and NK-cells).

The terms "hematopoietic progenitor cell", "hematopoietic progenitor", "hematopoietic precursor, or "HPC" as used interchangeably herein refer to cells which are derived from hematopoietic stem cells. HPCs are differentiated further than hematopoietic stem cells but have yet to differentiate into progenitors or precursors of respective blood cell lineages (unipotent precursor cells). Thus, HPCs are lineage-committed, i.e., an individual cell can give rise to progeny limited to a single lineage such as the myeloid or lymphoid lineage.

The terms "hematopoietic stem and progenitor cell" or "HSPC" as used interchangeably herein refers to both hematopoietic stem cells and hematopoietic progenitor cells.

The terms "hematopoietic syndrome" or "acute hematopoietic radiation syndrome" as used interchangeably herein refer to the reduction of hematopoietic cells following radiation exposure. Other symptoms of acute hematopoietic radiation syndrome include nausea, vomiting, diarrhea, mucositis, skin erythema, and fever. Persons suffering from acute hematopoietic radiation syndrome may also display impaired wound healing, bleeding, and anemia. Typically, acute hematopoietic radiation syndrome develops after radiation exposures exceeding 1 Gy.

A "normal" level, or "control" level, as used herein can be a level in a control population. A normal population is preferably a population of subjects having similar characteristics as the subject being treated, such as age. The "normal" level can also be a range of values, such as a range of acceptable values for levels of hematopoietic cells, HSCs, or HPCs.

A "pharmaceutically acceptable excipient," "pharmaceutically acceptable diluent," "pharmaceutically acceptable carrier," or "pharmaceutically acceptable adjuvant" as used interchangeably herein means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use, such as those promulgated by the United States Food and Drug Administration.

"Stem cells" as used herein refers to cells which are not terminally differentiated and are therefore able to produce cells of other types. Stem cells are divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are stem cells with the potential to make any differentiated cell in the body, but cannot contribute to making the extraembryonic membranes. "Multipotent stem cells" are clonal cells that self-renew as well as differentiate to regenerate adult tissues. "Multipotent stem cells" are also referred to as "unipotent" and can only become particular types of cells, such as blood cells or bone cells.

"Sample", "biological sample", or "test sample" as used interchangeably herein can mean any sample in which the presence and/or level of a target bacteria is to be detected. Samples may include a biological sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" and "patient" are used interchangeably herein. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. In some embodiments, the subject is human.

As used herein, the term "treat" or "treating" a subject refers to administering a disclosed composition to the subject to achieve a desired therapeutic effect. For example, treating a subject suffering from acute hematopoietic radiation syndrome refers to administering an effective amount of a disclosed composition to the subject such that at least one symptom of acute hematopoietic radiation syndrome is healed, alleviated, relieved, altered, remedied, ameliorated, or improved.

2. Methods of Promoting Regeneration of Hematopoietic Stem and Progenitor Cells Disclosed herein are methods of promoting regeneration of hematopoietic stem and progenitor cells in a subject in need thereof. The method may comprise administering to the subject a composition comprising a CaMKK2 inhibitor. Calmodulin (CaM) is the primary intercellular calcium sensor and binding to free cytosolic $Ca^{2+}$ causes conformational changes that facilitate its interaction with the multifunctional Ser/Thr kinases $Ca^{2+}$/CaM-dependent protein kinase I, IV (CaMKI and CaMKIV, respectively) and $Ca^{2+}$/CaM-dependent protein kinase kinase I (CaMKK1) and CaMKK2 to activate $Ca^{2+}$/CaM-dependent signaling cascades. CaMKK2 activation permits phosphorylation of CaMKI, CaMKIV and the adenosine monophosphate activated protein kinase (AMPK). The expression of CaMKK2 is relatively cell type restricted and outside the brain it is found in osteoblasts, macrophages, and myeloid progenitors.

a. CaMKK2 Inhibitors

The CaMKK2 inhibitor may be any agent that decreases the level and/or activity of CaMKK2. The CaMKK2 inhibitor may be any agent that inhibits the transcriptional or translational processes involved in CaMKK2 expression. For example, the CaMKK2 inhibitor may be an agent that inhibits transcription of CaMKK2 DNA. As another example, the CaMKK2 inhibitor may be an agent that inhibits the translation of CaMKK2 mRNA. The CaMKK2 inhibitor may be any suitable agent that diminishes CaMKK2 activity (e.g., reduces CaMKK2 signaling).

Suitable CaMKK2 inhibitors include small molecule inhibitors, antisense oligonucleotides, siRNA, miRNA, antibodies, and the like. For example, the CaMKK2 inhibitor may be a small molecule inhibitor. The CaMKK2 inhibitor may be 7H-benzimidazo(2,1-a)benz(de)isoquinoline-7-one-3-carboxylic acid (STO-609) or a derivative thereof.

As another example, the CaMKK2 inhibitor may be an antibody, antibody derivative, or antibody fragment that binds CaMKK2 with an overall inhibitory effect. For example, the CaMKK2 inhibitor may be an antibody, derivative, or fragment thereof that binds CaMKK2 to inhibit CaMKK2 signaling. The CaMKK2 inhibitor may be an antisense oligonucleotide. An antisense oligonucleotide refers to a stretch of single-stranded DNA or RNA whose sequence (3'-5') is complementary to the sense sequence of a molecule of mRNA. Antisense oligonucleotides may be chemically modified. Antisense molecules thereby effectively inhibit gene expression by forming RNA/DNA duplexes and physically blocking the ability of ribosomes to move along the messenger RNA. An antisense oligonucleotide need not have 100% identity with the complement of its target sequence in order to be effective. For example, antisense oligonucleotides may have a sequence that is at least about 70% identical to the complement of the target sequence. For example, antisense oligonucleotides may have a sequence that is at least about 70% identical, about 75% identical, about 80% identical, about 85% identical, about 90% identical, about 95% identical to the complement of the target CaMKK2 sequence, allowing for gaps or mismatches of several bases.

Other suitable examples of methods that may be used to achieve inhibition of CaMKK2 include RNA interference (RNAi). RNA interference describes a biological process in which RNA molecules inhibit gene expression by neutralizing targeted mRNA molecules. RNAi may be mediated by any suitable inhibitory RNA, such as a dsRNA, a siRNA, a piRNA, an antisense RNA, a ribozyme, a RNAse external guide sequence, a miRNA, or a shRNA. For example, the CaMKK2 inhibitor may be an siRNA designed to inhibit expression of CaMKK2.

b. Modes of Administration

The composition may further comprise one or more pharmaceutically acceptable carriers. The type of carrier to be used depends on the form of the composition and the mode of administration to be used. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants.

Compositions may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Compositions suitable for oral administration (e.g. by ingestion) may be presented as discrete units such as capsules, cachets or tablets, each containing a predetermined amount of the active compound; as a powder or granules, as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Compositions suitable for parenteral administration (e.g. by injection, including cutaneous, subcutaneous, intramuscular, intravenous and intradermal), include aqueous and nonaqueous isotonic, pyrogen-free, sterile injection solutions which may contain anti-oxidants, buffers, preservatives, stabilizers, bacteriostats, and solutes which render the composition isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such compositions include Sodium Chloride Injection, Ringer's Solution, or Lactated Ringer's Injection. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Compositions may be in the form of liposomes or other microparticulate systems which are designed to target the active compound to blood components or one or more organs.

Compositions suitable for topical administration (e.g. transdermal, intranasal, ocular, buccal, and sublingual) may be formulated as an ointment, cream, suspension, lotion, powder, solution, past, gel, spray, aerosol, or oil. Alternatively, a composition may comprise a patch or a dressing such as a bandage or adhesive plaster impregnated with active compounds and optionally one or more excipients or diluents.

Compositions suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Compositions suitable for topical administration to the eye also include eye drops wherein the active compound is dissolved or suspended in a suitable carrier, especially an aqueous solvent for the active compound.

Compositions suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable compositions wherein the carrier is a liquid for administration as, for example, nasal spray, nasal drops, or by aerosol administration by nebulizer, include aqueous or oily solutions of the active compound.

Compositions suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases. Further compositions suitable for inhalation include those presented as a nebulizer.

Compositions suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical compositions may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream compositions.

Suitable emulgents and emulsion stabilizers include Tween 60, Span 80, cetostearyl alcohol, myristyl alcohol, glyceryl monostearate and sodium lauryl sulfate. The choice of suitable oils or fats for the composition is based on achieving the desired cosmetic properties, since the solubility of the active compound in most oils likely to be used in pharmaceutical emulsion compositions may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Compositions suitable for rectal administration may be presented as a suppository with a suitable base comprising, for example, cocoa butter or a salicylate.

Compositions suitable for vaginal administration may be presented as pessaries, tampons, creams, gels, pastes, foams or spray compositions containing in addition to the active compound, such carriers as are known in the art to be appropriate.

c. Regeneration of HSPCs

The disclosed CaMKK2 inhibitor compositions may be administered to promote regeneration of HSPCs in a subject in need thereof. The subject in need thereof may have a bone marrow injury. The bone marrow injury may be any injury that causes a hematopoietic deficiency in the subject. For example, the bone marrow injury may be any injury that causes reduced levels of HSPCs in the subject. For example, the bone marrow injury may be caused by chemotherapy, radiation, blood loss, or infection. Reduced levels of HSPCs in the subject may refer to reduced levels or HSCs, reduced levels of HPCs, or both. Administration of the disclosed compositions may promote regeneration of HSPCs in the subject. Regeneration of HSPCs in the subject may refer to regeneration of HSCs, regeneration of HPCs, or both.

Successful regeneration of HSPCs in the subject may be indicated by increased levels of HSCs, HPCs, or both in the bone marrow of the subject. Successful regeneration of HSPCs in the subject may also be indicated by increased levels of any type of hematopoietic cell in the subject. For example, successful regeneration of HSPCs in the subject may cause elevated levels of blood cells from the myeloid (monocyte, macrophases, neutrophils, basophils, eosinophils, erythrocytes, platelets and dendritic cells) lineages. Successful regeneration of HSPCs in the subject may cause elevated of blood cells from the lymphoid lineages (T-cells, B-cells and NK-cells). Suitable methods for measuring levels of these cells in the subject are known in the art.

In some embodiments, the subject may be undergoing forms of treatment for cancer. These forms of treatment, such as radiation therapy or chemotherapy, may cause bone marrow injury in the subject. For example, the bone marrow injury may be caused by chemotherapy. The bone marrow injury may be caused by radiation. For example, the bone marrow injury may be caused by total body irradiation. The disclosed compositions comprising a CaMKK2 inhibitor may be administered to the subject before, concurrently with, or following cancer treatment to promote regeneration of HSPCs in the subject.

In some embodiments, the subject may have or may be at risk of developing acute hematopoietic radiation syndrome. For example, administration of chemotherapy or radiation therapy may cause acute hematopoietic radiation syndrome in the subject. Alternatively, administration of chemotherapy or radiation therapy may put the subject at risk of developing acute hematopoietic radiation syndrome. The disclosed compositions may be administered to the subject to treat or prevent acute hematopoietic radiation syndrome in the subject. For example, the disclosed compositions may be administered to the subject before, concurrently with, or after radiation therapy or chemotherapy to treat or prevent acute hematopoietic radiation syndrome in the subject. Successful treatment of acute hematopoietic radiation syndrome in the subject may be indicated by an improvement in one or more symptoms of acute hematopoietic radiation syndrome in the subject. For example, successful treatment may be indicated by increased levels of one or more hematopoietic cells in the subject, including HPCs and/or HSPCs.

Any suitable dosage of the CaMKK2 inhibitor may be used to promote regeneration of HSPCs in the subject. It will be appreciated that appropriate dosages of the CaMKK2 inhibitor, and compositions comprising the CaMKK2 inhibitor, can vary from patient to patient. Determining the optimal dosage will generally involve the balancing of the level of therapeutic benefit against any risk or deleterious side effects of the treatments. The selected dosage level will depend on a variety of factors including, but not limited to, the activity of the particular CaMKK2 inhibitor, the route of administration, the time of administration, the rate of excretion of the CaMKK2 inhibitor, the duration of the treatment, other drugs, compounds, and/or materials used in combination, and the age, sex, weight, condition, general health, and prior medical history of the patient.

In general, a suitable dose of the CaMKK2 inhibitor is in the range of about 1 µg/kg body weight to about 250 mg/kg body weight of the subject per day. For example, a suitable dose of the CaMKK2 inhibitor may be 1 µg/kg to about 250 mg/kg, 10 µg/kg to about 200 mg/kg, about 100 µg/kg to about 150 mg/kg, about 1 mg/kg to about 100 mg/kg, about 2.5 mg/kg to about 50 mg/kg, about 5 mg/kg to about 25 mg/kg, or about 10 mg/kg to about 15 mg/kg. For example, a suitable dosage of the CaMKK2 inhibitor may be about 1 mg/kg to about 1 mg/kg to about 100 mg/kg, about 2 mg/kg to about 50 mg/kg, about 3 mg/kg to about 25 mg/kg, or about 4 mg/kg to about 10 mg/kg. For example, a suitable dosage of the CaMKK2 inhibitor may be about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

The composition may be administered to the subject once a day, or multiple times over the course of the day. For example, the composition may be administered to the subject in a single dose once per day. As another example, the composition may be administered to the subject twice per day, three times per day, four times per day, or five times per day. The composition may be administered to the subject for any suitable duration of time necessary to achieve the desired result. For example, the composition may be administered to the subject for at least 1 day, at least 2 days, at least 3 days, at least 4 days, at least 5 days, at least 6 days, at least 1 week, at least 2 weeks, at least 3 weeks, at least 1 month, at least 2 months, at least 3 months, or at least 6 months.

The methods of the invention will be better understood by reference to the following examples, which are intended as an illustration of and not a limitation upon the scope of the invention.

3. Examples

The following Examples are offered as illustrative as a partial scope and particular embodiments of the disclosure and are not meant to be limiting of the scope of the disclosure.

Example 1

Materials and Methods

Mice:

CaMKK2-EGFP transgenic reporter mice were used. Radiation was delivered by a Shepherd Cs$^{137}$γ-irradiator at a dose rate of approximately 600 cGy per min. All animal experiments were performed according to protocols approved by the Duke University Institutional Animal Care and Use Committee.

Antibodies:

Anti-CaMKK (pan-KK) was from BD Biosciences (San Jose, Calif., USA), anti-phospho-S6rp$^{S240/244}$, anti-phospho-AMPKα$^{T172}$ and anti-AMPKα were from Cell Signaling Technology (Danvers, Mass., USA). Anti-phospho-CaMK1$^{T177}$ was from Santa Cruz Biotechnology (Dallas, Tex., USA). Anti-β-actin was from Sigma.

M1 Cells and Proliferation Assay:

M1 cells (ATCC TIB-192) were obtained from Duke Cell Culture Facility (Durham, N.C., USA). In proliferation experiments, M1 cells were seeded at $2 \times 10^4$/ml per well into a 24-well plate. MTS Cell Proliferation Assay Kit was from Abcam (Cambridge, Mass., USA).

Isolation and FACS of HSPC:

HSPC were sorted from mouse BM based on surface expression of c-Kit, Sca-1, and low to negative expression of lineage markers (lin$^-$). KSL CD34$^-$ were used in reconstitution experiments. All antibodies were purchased from BD Biosciences, BioLegend (San Diego, Calif., USA) or eBioscience (Waltham, Mass., USA). Annexin-V/7AAD apoptosis kit was from BD Biosciences. The cell sorting and analyses were performed on a FACSVantage cell sorter or CANTO analyzer (Becton Dickinson, Franklin Lakes, N.J., USA).

Microarray Analysis:

KLS cells were sorted from BM directly into Buffer RLT (Qiagen, Frederick, Md., USA). Microarray analysis was performed at Sequencing and Genome Technologies Shared Resource (Duke University). Microarray data are available at GEO (accession number: GSE95733).

Gene Set Enrichment Analysis:

Gene set enrichment analysis (GSEA) was applied to our microarray data. All genes were ranked by the fold change between the Camkk2 null and WT control samples. Normalized enrichment score (NES) and adjusted q-values were computed utilizing the GSEA method, based on 1000 random permutations of the ranked genes. Gene set collections (MSigDB) was used to determine enriched pathways.

In Vivo Transplantation Experiments:

For competitive engraftment assays, the total BM cells were isolated from femurs and tibiae of WT and Camkk2 null (CD45.2 background). c-Kit-positive cells were enriched using anti-CD117/c-Kit microbeads (Miltenyi Biotec, Auburn, Calif., USA). The KSL CD34$^-$ stem cells (CD45.2) were then sorted and 1000 cells were injected with $5 \times 10^5$ competitor whole BM (CD45.1) into lethally irradiated (split dose totaling 10 Gy) recipient B6-CD45.1 (B6.SJL-Ptprca Pepcb/BoyJ) mice via the retro-orbital sinus. In the same experiments, KSL CD34$^-$ cells were sorted from BM of Camkk2 null or control mice treated with 200 cGy 90 days before transplant. For lineage analysis, peripheral blood cells were collected and prepared. In some experiments, transplanted mice were monitored for up to 4 months, and then mice received 450 cGy TBI. Mice were finally monitored for chimerism.

In Vitro Proliferation with Endothelial Cells and Methylcellulose Assays:

Primary BMECs were generated. For liquid culture experiments, freshly sorted KSL cells from control or Camkk2 null mice were plated in 2% FCS-medium (X-Vivol 5, Lonza, Portsmouth, N.H., USA) supplemented with 50 μM 2-mercaptoethanol, SCF (50 ng/ml) and Flt-3 (30 ng/ml). After culturing for the indicated time, live cells were counted using Trypan blue exclusion. For methylcellulose assays, the recovered cells were plated in complete methylcellulose medium (StemCell Technologies, Vancouver, BC, Canada, catalog number M3434). The colony numbers were counted 8-10 days after plating.

Immunofluorescence Staining of Bone Sections:

Femurs were decalcified, embedded in OCT media (Sakura Finetek, Torrance, Calif., USA) and 10 μm sections were cut using the CryoJane tape system (Instrumedics Inc., Hackensack, N.J., USA). To assess BM cellularity, sections were stained with hematoxylin/eosin. Vasculature and EGFP+ cells were identified with anti-mouse VE-Cadherin (Abcam) and anti-GFP antibodies (Abcam). The nuclear dye DAPI (Invitrogen, Waltham, Mass., USA) was included in all stains. Images were obtained using an Axiovert 200 microscope (Carl Zeiss, Thornwood, N.Y., USA).

Immunoblotting:

Immunoblots were performed and visualized on an Odyssay CLx imager (LI-COR Biosciences, Lincoln, Nebr., USA). Image Studio software (Lincoln, Nebr., USA) was used for quantitation.

ShRNA Lentivirus:

shRNA3145 (TRCN0000028776) against Camkk2 and the negative control pLKO (TRCN0000241923) were obtained from Open Biosystems (Huntsville, USA). M1 cells were infected with shRNA3145 or pLKO virus containing sham shRNA pLKO vector, or Camkk2 (3142, 3143 or 3145 clones) shRNA vector using polybrene as per the manufacturer's instruction. Cells were then selected and maintained in media with puromycin.

Statistical Analysis:

In mice studies, a power calculation of sample size was performed with the help of the Duke University Biostatistic core service. A two-tailed Student's t-tests and one-way ANOVA were used to determine statistical significance. A P-value<0.05 was considered significant. The variance was comparable between each group of data that was statistically compared. The statistical significance was determined using GraphPad Prism 7 software (GraphPad Software, Inc., La Jolla, Calif., USA).

Pathway Analysis:

iPathwayGuide® (IPG) software use the impact analysis method with Bonferroni correction. Briefly, this method uses two types of evidence: i) the over-representation of differentially expressed (DE) genes in a given pathway and ii) the perturbation of that pathway computed by propagating the measured expression changes across the pathway topology. These aspects are captured by two independent probability values, pORA and pAcc, that are then combined in a unique pathway-specific p-value. The underlying pathway topologies, comprised of genes and their directional interactions, are obtained from the KEGG database.

RNA Isolation and Real-Time PCR:

Total RNAs were isolated using QIAquick PCR purification kit (Qiagen, Valencia, Calif.). Single-stranded cDNA was synthesized using SuperScript II reverse transcriptase (Invitrogen) according to the manufacturer's directions and protocol described previously 1. Real-time PCRs were performed using an iCycler (Bio-Rad) with the IQ SYBR Green supermix (Bio-Rad). After deriving the relative amount of each transcript from a standard curve, transcript levels were normalized to GAPDH. PCR primers were from Qiagen (RT2 quantitative PCR primer assays, SAbiosciences).

Sto-609 Administration:

STO-609 was purchased from TOCRIS Bioscience. Stock solution of 20 mM was made in 100 mM NaOH (Sigma, St. Louis, Mo.). STO-609 stock of 20 mM was diluted 1:2000 in sterile saline solution to obtain a 10 µM working stock concentration. 200 µL of 10M STO-609 was administered intravenously for in-vivo experiments.

Example 2

CaMKK2 Expression is Enriched in HSPC In Vivo

CaMKK2-enhanced green fluorescent protein (EGFP) mice were used to determine the location and phenotype of Camkk2-expressing cells within the BM microenvironment. The analysis of reporter bone sections by immunofluorescence revealed activity in individual single cells throughout the BM (FIG. 1A). A subset of EGFP-positive cells was located adjacent to the vascular endothelial marker VE-cadherin (FIGS. 1Ac-d, high-magnification inset). Approximately 20% of lineage (Lin)+ cells were EGFP positive by flow cytometry. The reporter was active in 25-40% of Lin$^-$cKit$^-$ (CD117) stem cell antigen-1– (Sca$^-$) cells and 5-10% of the Lin$^-$cKit$^-$Sca$^+$ cells. Conversely, the EGFP reporter was detectable in 95-100% of Lin$^-$cKit$^+$ cells (FIGS. 1B, 1C). A detailed analysis of the HSPC compartment revealed robust reporter activation in Lin$^-$cKit$^+$Sca$^-$ (KL) and Lin$^-$cKit$^+$Sca$^+$ (KSL) cells (FIGS. 1B, 1C, top panels). Additional KSL subset analyses using the signaling lymphocyte activation molecules (SLAM) markers CD150 and CD48 showed EGFP expression in the LT-HSC population defined as KSL CD150$^+$CD48$^-$ and multipotent progenitors (MPP, KSL CD150$^-$CD48$^-$; FIGS. 1B, 1C, bottom panels). The reporter was highly active in committed hematopoietic progenitor populations 1 and 2 (HPC-1 and HPC-2) defined as KSL CD150$^-$CD48$^+$ and CD150$^+$CD48$^+$ (FIGS. 1B, 1C, bottom panels). Cumulatively, these data suggest the capacity to initiate Ca$^2$-dependent signaling via CaMKK2 is enriched in the most primitive hematopoietic stem cells.

Example 3

CaMKK2 Regulates the HSPC Transcriptional Program

Figure 2A:
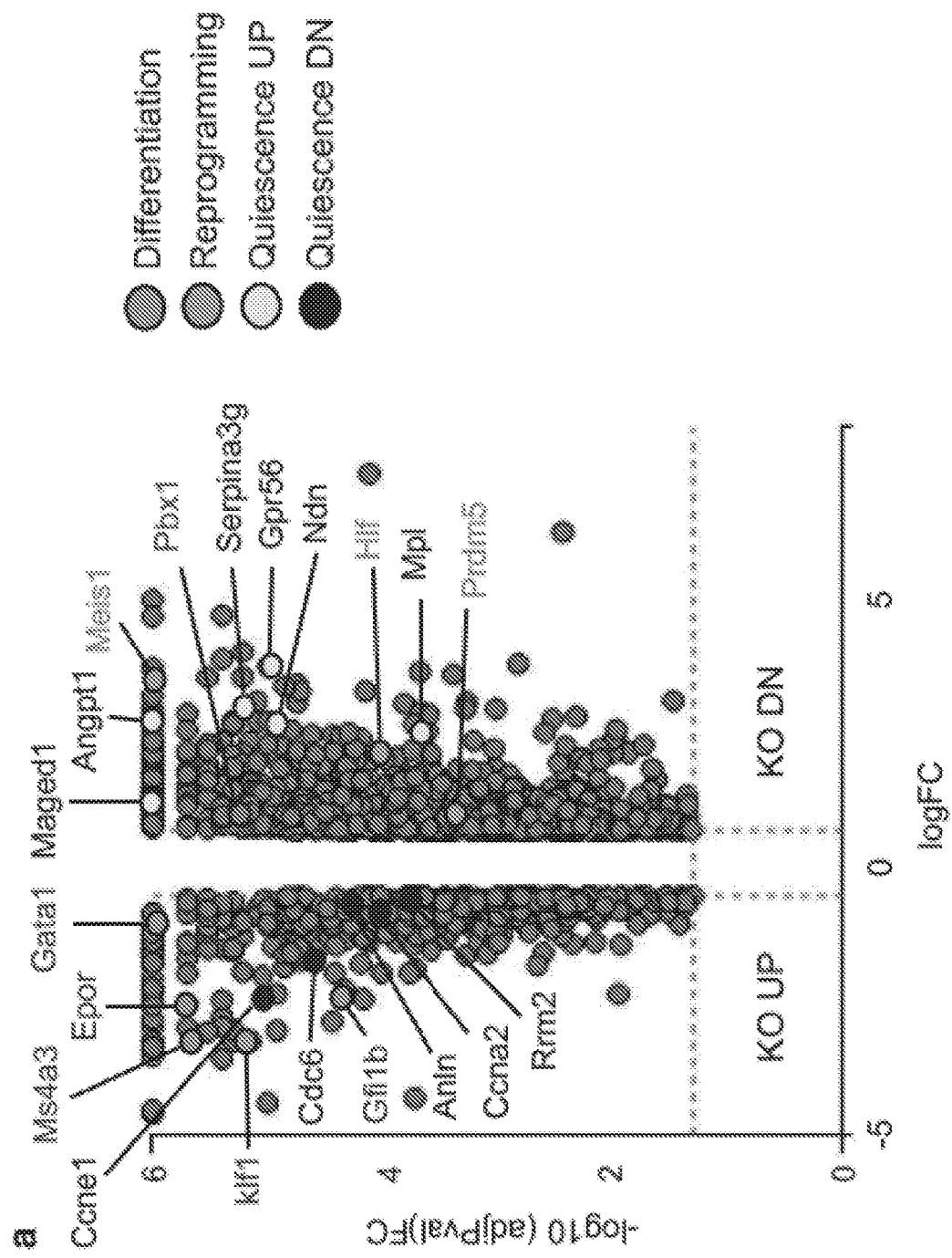
Figure 2B:
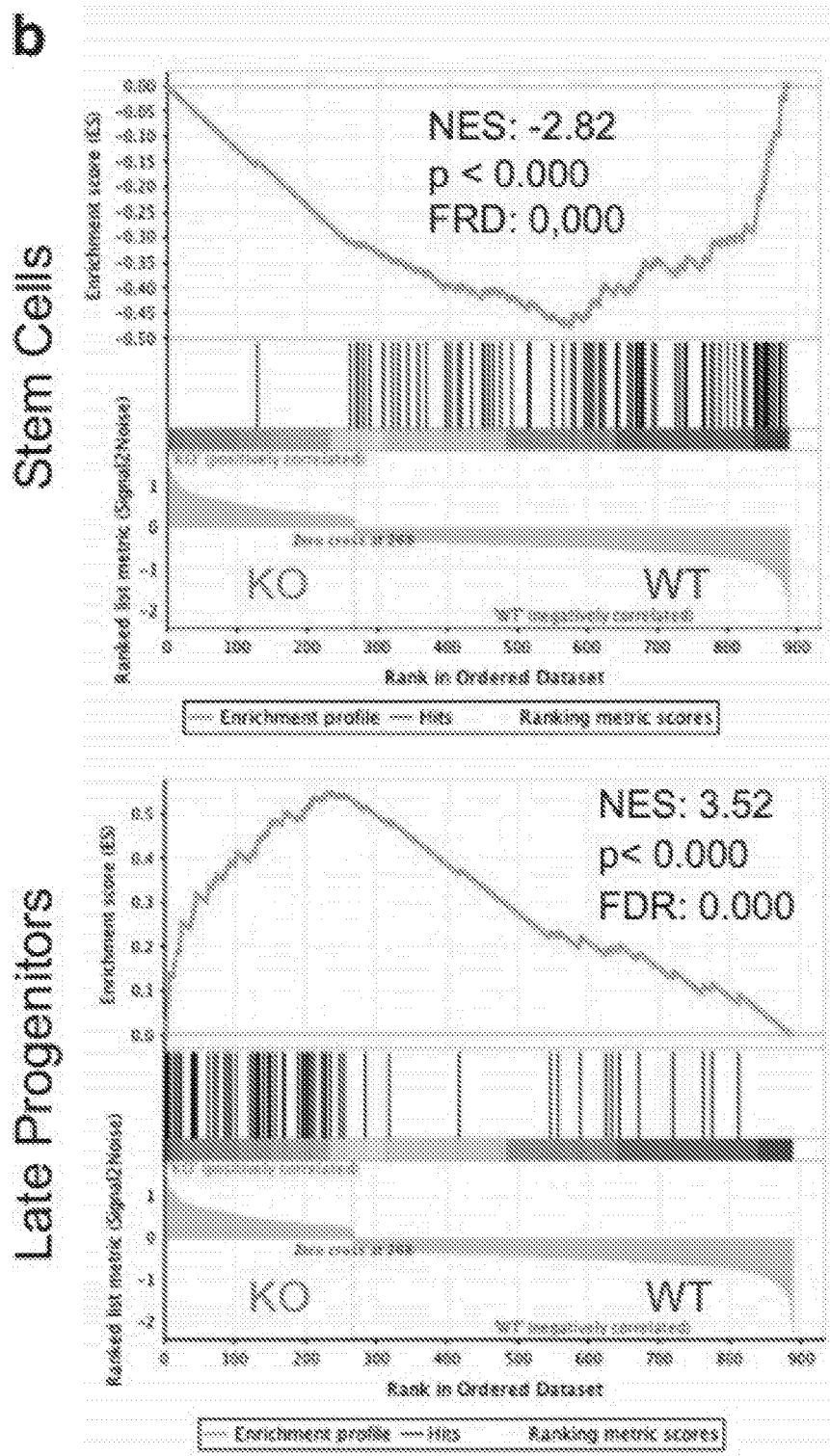

To identify gene sets controlled by Camkk2 in HSPC, microarray analyses were performed on KSL cells isolated from WT and Camkk2 null mice. Results show that 1289 genes were significantly downregulated and 533 genes were upregulated in Camkk2 null KSL compared with WT (FIG. 2A). The lists of the top differentially expressed genes (DEGs) are reported in Table 1 and Table 2. The gene set enrichment analysis (GSEA) showed genes downregulated in Camkk2 null KSL were enriched in HSC, early progenitors, and lymphoid-myeloid-affiliated genes (s-myly) primed in HSC (FIG. 2B, upper panel; FIG. 8A). The HSC-affiliated downregulated genes in Camkk2 KSL included Hlf, Meis1, Pbx-1 and Prdm5. These genes represent four of the eight genes capable of reprogramming committed murine blood cells into HSC (FIG. 2A). Conversely, genes affiliated with the late progenitor signature (FIG. 2B, lower panel), erythroid genes primed in HSC, and granulocyte macrophage progenitor (GMP)-specific genes (d-my) were significantly upregulated in Camkk2 null KSL (FIGS. 8B, 8C).

Figure 2C:
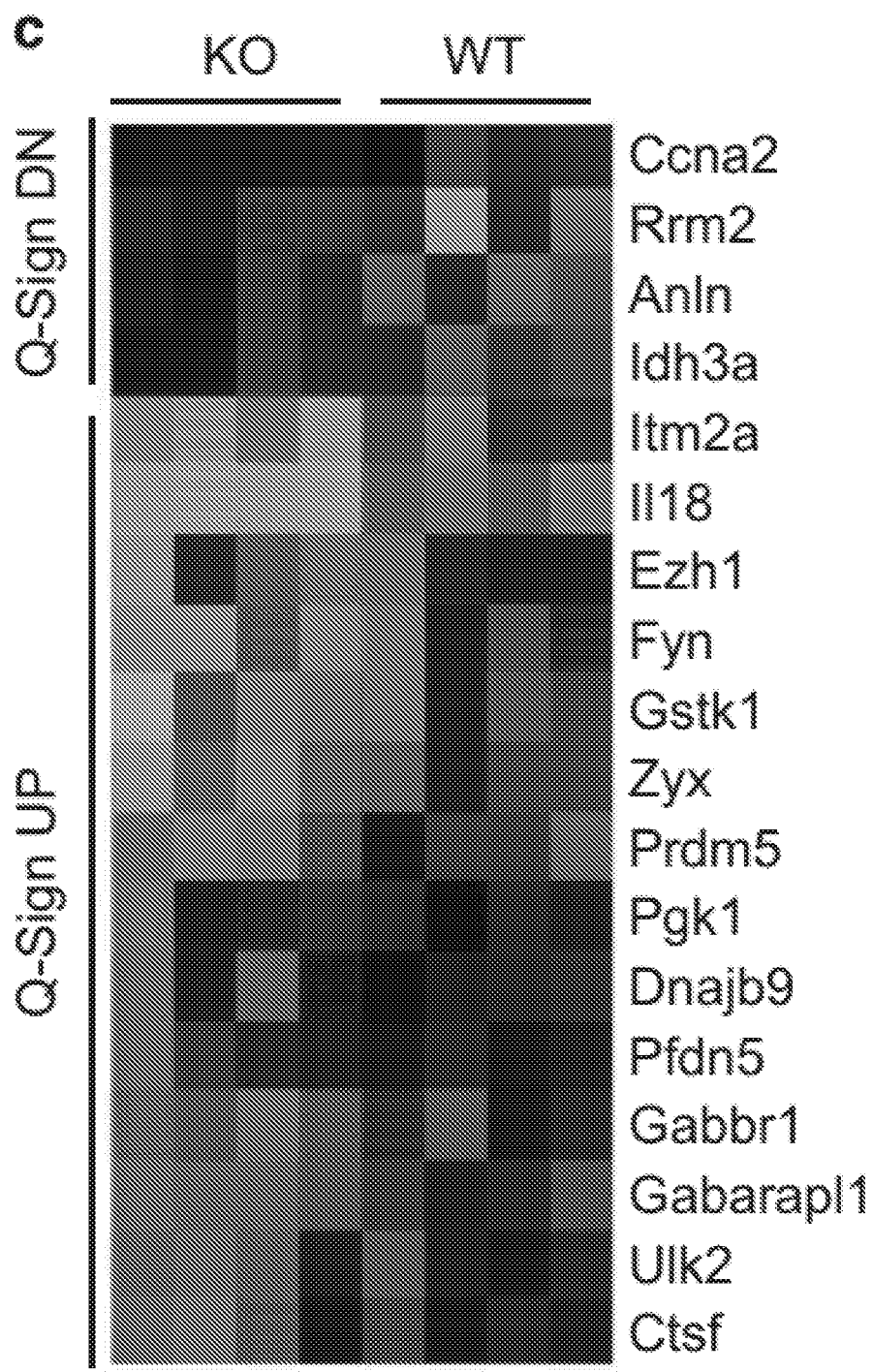

The pathways over represented by Camkk2 null KSL DEGs included cell adhesion molecules (CAMs, P=8.218e-8) and chemokine signal pathway (P=0.0275; Table 2). The gene expression affiliated with the quiescent signature was analyzed in various stem cells including hematopoietic, muscle and hair follicle stem cells. Results show that 25% (18 of 71) of genes affiliated with a quiescent stem cell signature (Q-Sign) were differentially expressed in Camkk2 null KSL. Interestingly, 14 of 49 genes upregulated in Q-Sign (Q-Sign UP) were downregulated in Camkk2 KO KSL (FIG. 2C). Moreover, none of the Q-Sign UP genes were upregulated in Camkk2 null KSL (FIG. 2C, P=0.0144). None of the 22 genes downregulated in quiescent stem cells (Q-Sign DN) were downregulated in Camkk2 null KSL. In contrast, four Q-Sign DN genes (Ccna2, Rrm2, Anln and Idh3) were upregulated in Camkk2 null compared with WT KSL (FIG. 2C; P-value=0.0075). This finding was corroborated using gene signatures specifically affiliated with HSC quiescence and proliferative status (HQ-sign and HP-sign, respectively). Results show that 15% of HQ-sign genes (40 of 264) were significantly downregulated in Camkk2 null KSL. However, only 3 of 264 genes were significantly upregulated in Camkk2 null KSL (FIGS. 9A-C; P=0.0001). The data indicate 12 of 313 genes in the HP-Sign were upregulated in Camkk2 null KSL compared with WT and 3 of 264 were downregulated in Camkk2 null KSL (FIGS. 9A-B; P=–0.0632). Collectively, these findings indicate the deletion of Camkk2 downregulates genes controlling HSPC quiescence and concurrently upregulates genes affiliated with the late progenitor signature.

TABLE 1

Differentially Expressed Genes in Camkk2$^{-/-}$ KSL

| symbol | logfc | adjpv |
|---|---|---|
| Genes up-regulated in Camkk2$^{-/-}$ KSL | | |
| Cldn13 | −4.596835549 | 0.000001 |
| Ahsp | −4.538389152 | 0.000001 |
| Rhag | −4.406597289 | 0.00001 |
| S100a8 | −4.312676557 | 0.000187 |
| Aqp1 | −3.596490005 | 0.000004 |
| Ces2g | −3.546739687 | 0.000001 |
| Ermap | −3.405521353 | 0.000001 |
| Gm5843 | −3.382014562 | 0.000001 |
| Slc38a5 | −3.281662813 | 0.000001 |
| Klf1 | −3.274878015 | 0.000007 |
| Rhd | −3.271468275 | 0.000005 |
| Nxpe2 | −3.26499576 | 0.000001 |
| Tspan8 | −3.107273648 | 0.000003 |
| Gm15915 | −3.080532875 | 0.000012 |
| Trem3 | −3.064325065 | 0.000005 |
| Fam132a | −3.022374205 | 0.000002 |
| Car1 | −3.017982882 | 0.000001 |
| Ms4a3 | −3.007166651 | 0.000004 |
| Ly6c2 | −2.908539062 | 0.000036 |
| Slc25a21 | −2.86505395 | 0.000001 |
| Atp1b2 | −2.825536897 | 0.000004 |
| Tspan33 | −2.622492313 | 0.000001 |
| Epor | −2.604909442 | 0.000002 |

TABLE 1-continued

Differentially Expressed Genes in Camkk2$^{-/-}$ KSL

| symbol | logfc | adjpv |
|---|---|---|
| Cpox | −2.552565298 | 0.000001 |
| Mt1 | −2.516082267 | 0.000004 |
| Ccne1 | −2.501435952 | 0.000009 |
| Snora73b | −2.496505786 | 0.000067 |
| Ctse | −2.409644165 | 0.011323 |
| Elane | −2.403334996 | 0.000012 |
| Paqr9 | −2.403334996 | 0.000048 |
| Kel | −2.385086315 | 0.000001 |
| Snora73a | −2.33020026 | 0.000047 |
| Hmbs | −2.306577114 | 0.000001 |
| Asns | −2.297572551 | 0.000001 |
| Ppap2a | −2.109000344 | 0.000001 |
| Gypa | −2.073171929 | 0.000009 |
| Spire1 | −2.029463172 | 0.000002 |
| Igsf6 | −2.028148247 | 0.000168 |
| Stom | −2.0255132 | 0.000038 |

Genes Down-regulated in Camkk2$^{-/-}$ KSL

| symbol | logfc | adjpv |
|---|---|---|
| Ighv1-2 | 7.152511583 | 0.000076 |
| Igkv19-93 | 6.08258414 | 0.003751 |
| Dntt | 4.834295809 | 0.000001 |
| Ighm | 4.548811452 | 0.000004 |
| Gm19590 | 4.532707014 | 0.000001 |
| Eltd1 | 3.883417748 | 0.000006 |
| Gcnt2 | 3.745259788 | 0.000004 |
| Igh-VJ558 | 3.659708077 | 0.001526 |
| Ctla2b | 3.606041176 | 0.00001 |
| Gm5111 | 3.579622468 | 0.000001 |
| Igkv4-59 | 3.507357577 | 0.000208 |
| Ighv1-77 | 3.458522448 | 0.000417 |
| Insl6 | 3.410157123 | 0.000006 |
| Flt3 | 3.405853193 | 0.000003 |
| Ctla2a | 3.280535205 | 0.000018 |
| Ighv11-1 | 3.244543572 | 0.000014 |
| Igkv4-54 | 3.153163282 | 0.00007 |
| Igkv4-62 | 3.152308581 | 0.000019 |
| Myct1 | 3.07176696 | 0.000001 |
| Igkv8-30 | 2.980618636 | 0.033687 |
| Gpr56 | 2.976549454 | 0.000008 |
| Igj | 2.955430977 | 0.000546 |
| Igkv4-57 | 2.939161922 | 0.000018 |
| Laptm4b | 2.924773185 | 0.000152 |
| Meis1 | 2.838493497 | 0.000001 |
| Ighv1-73 | 2.832036181 | 0.000539 |
| Ighv1-55 | 2.83085763 | 0.000978 |
| Igkv4-55 | 2.777576264 | 0.000211 |
| Cd34 | 2.740194654 | 0.000002 |
| Igkv4-61 | 2.730463796 | 0.000258 |
| Rbp1 | 2.696652156 | 0.000001 |
| Ighv1-5 | 2.690564887 | 0.0049 |
| H2-Ob | 2.677590994 | 0.000001 |
| Ifi44 | 2.63905733 | 0.003045 |
| Sox4 | 2.618125494 | 0.000001 |
| Tmem176b | 2.616665639 | 0.000001 |
| 9030619P08Rik | 2.607861474 | 0.000005 |
| Igkv4-57-1 | 2.606386547 | 0.000214 |
| Angpt1 | 2.605648267 | 0.000001 |
| Serpina3g | 2.605648267 | 0.00001 |

TABLE 2

Pathway Analysis

| pName | pv_Bonferroni |
|---|---|
| Lysosome | 7.92E-10 |
| Hematopoietic cell lineage | 7.73E-08 |
| Cell adhesion molecules (CAMs) | 8.22E-08 |
| Metabolic pathways | 5.73E-07 |
| Phagosome | 2.08E-05 |
| Natural killer cell mediated cytotoxicity | 6.41E-05 |
| Fc gamma R-mediated phagocytosis | 0.000116349 |
| Antigen processing and presentation | 0.000133403 |
| Pathways in cancer | 0.000158135 |
| Tuberculosis | 0.000437487 |
| Fc epsilon RI signaling pathway | 0.000504321 |
| Leishmaniasis | 0.000580196 |
| Cytokine-cytokine receptor interaction | 0.000777057 |
| Transcriptional misregulation in cancer | 0.000792215 |
| *Staphylococcus aureus* infection | 0.00098973 |
| FoxO signaling pathway | 0.001262219 |
| Viral myocarditis | 0.001352085 |
| Toxoplasmosis | 0.001699385 |
| Inflammatory bowel disease (IBD) | 0.002013243 |
| Influenza A | 0.002205047 |
| Hepatitis B | 0.002251295 |
| Herpes simplex infection | 0.002351594 |
| Apoptosis | 0.002375065 |
| HTLV-I infection | 0.00267446 |
| Glutathione metabolism | 0.002954605 |
| Type I diabetes mellitus | 0.003012121 |
| Rheumatoid arthritis | 0.003049457 |
| Graft-versus-host disease | 0.003508518 |
| B cell receptor signaling pathway | 0.003607519 |
| Allograft rejection | 0.003775925 |
| T cell receptor signaling pathway | 0.003837721 |
| Jak-STAT signaling pathway | 0.00404303 |
| Osteoclast differentiation | 0.004059177 |
| Leukocyte transendothelial migration | 0.005472502 |
| Chagas disease (American trypanosomiasis) | 0.006290182 |
| Sphingolipid signaling pathway | 0.008017898 |
| Viral carcinogenesis | 0.011033526 |
| Measles | 0.012717421 |
| Central carbon metabolism in cancer | 0.013339102 |
| Ras signaling pathway | 0.017951374 |
| Systemic lupus erythematosus | 0.020248129 |
| ABC transporters | 0.021274373 |
| MAPK signaling pathway | 0.021903743 |
| Chemokine signaling pathway | 0.027561406 |
| Intestinal immune network for IgA production | 0.036701637 |

Example 4

Camkk2 Null HSPC have Increased Proliferation In Vitro

Figures 3A, 3B, 3C, 3D:
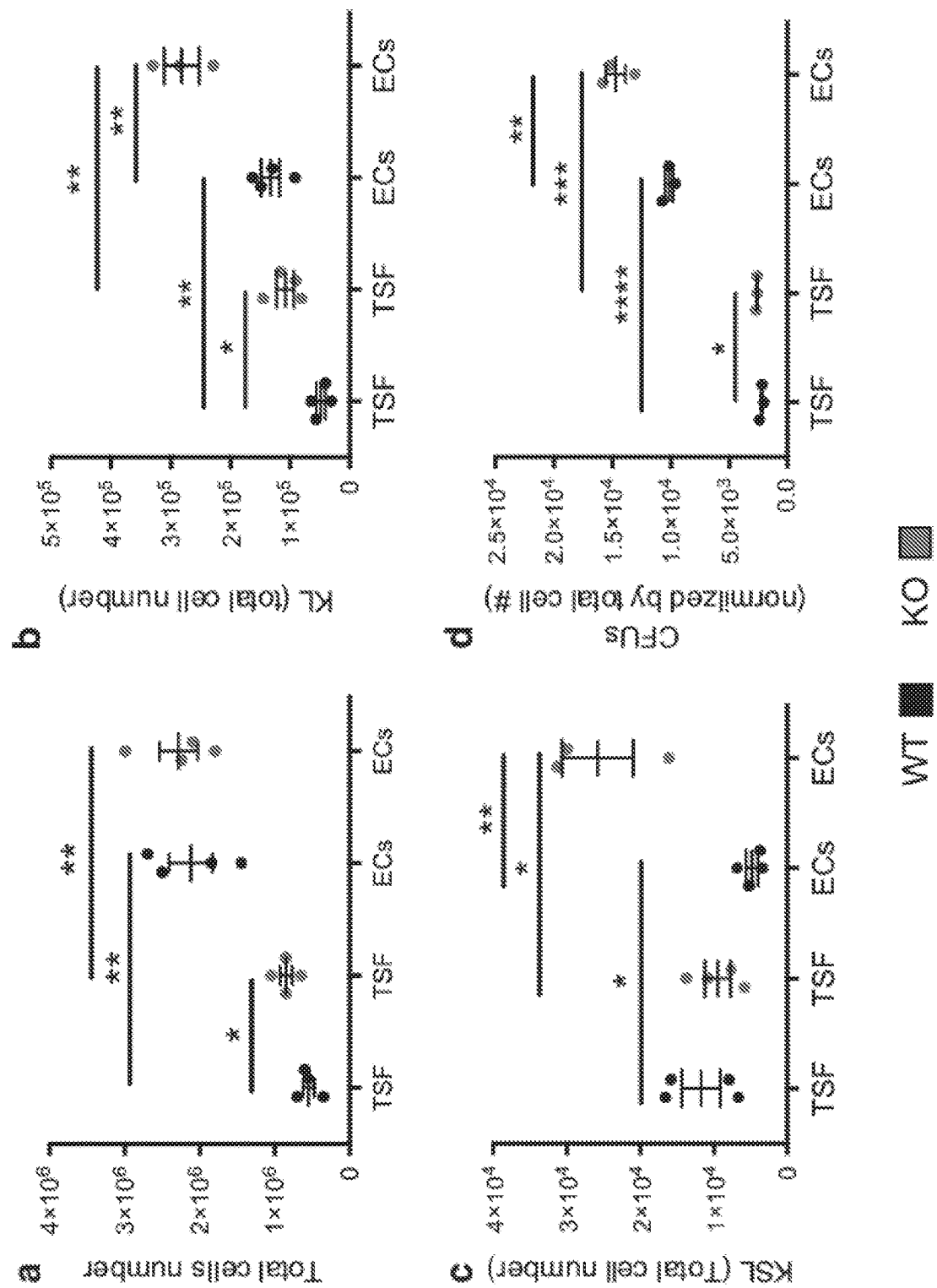

KSL cells sorted from control and Camkk2 null mice were cultured with thrombopoietin, SCF and Flt-3-ligand cytokines (TSF) to analyze the effect of Camkk2 ablation on HSPC proliferation in response to cytokines. In addition, the vascular niche microenvironment was mimicked using non-contact cultures with primary BM-derived endothelial cells (BMECs). After 7 days, the numbers of total KL and KSL cells were assessed. The cells recovered from cultures were then functionally analyzed in methylcellulose cultures to examine colony-forming unit (CFU) capacity. Regardless of the genotype, significantly more total cells were recovered from co-culture with BMEC compared with TSF alone (FIG. 3A). There was a slight increase in the numbers of total and KL cells found in TSF cultures of Camkk2 null KSL compared with WT cells (FIGS. 3B, 3C) Interestingly, the presence of BMEC resulted in a more robust increase in both KL and KSL recovered from Camkk2 null KSL compared with WT cultures (FIGS. 3B, 3C). The progeny derived from Camkk2 null KSL cultured in the presence of TSF had a modest increase in functional colony formation compared with WT cells (FIG. 3D). In contrast, progeny derived from Camkk2 null KSL cultured in the presence of BMEC generated a significantly higher number of CFUs compared with WT (FIG. 3D). Cumulatively, these results show Camkk2 null KSL cells have significantly higher proliferative ability than WT cells in culture conditions mimicking the hematopoietic niche.

Example 5

Camkk2 Null Mice have Improved Survival and Accelerated Hematopoietic Recovery Following Total Body Irradiation (TBI)

Figure 4A:
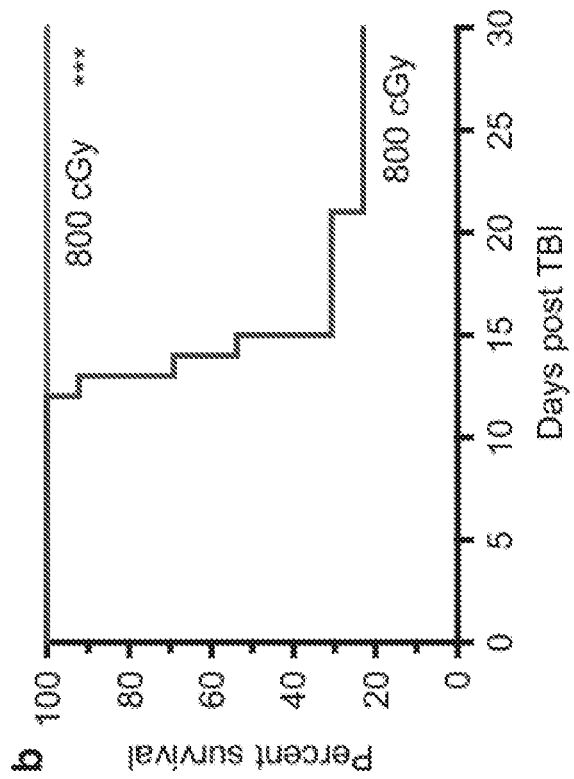

Under homeostatic conditions, Camkk2 ablation does not affect survival and proliferation of the KSL population in vivo. However, Camkk2 null HSPC have an increased ability to proliferate in vitro (FIG. 3) Therefore, it was hypothesized that CaMKK2 restrains the proliferation of HSPC. Thus, Camkk2 ablation would accelerate the hematological recovery following BM damage. To test this hypothesis, the hematopoietic compartment was injured in vivo using total body γ-irradiation (TBI; 700-900 cGy) and then mice were monitored for survival, blood counts, and BM recovery (FIG. 4A).

Figure 4B:
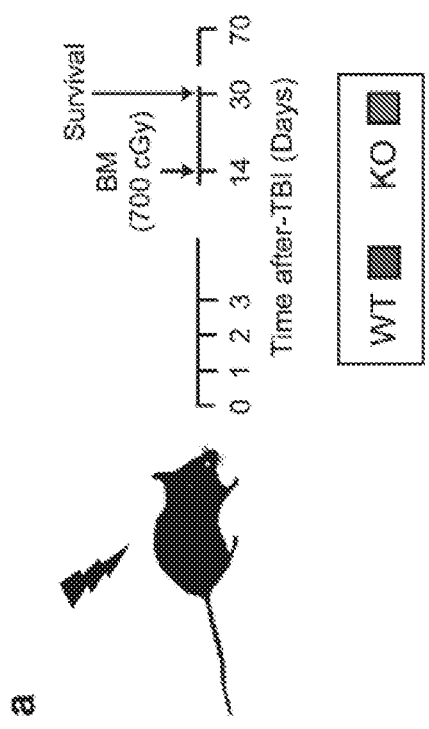

Using a single dose of 800 cGy TBI, which is sufficient to kill approximately 80% of control animals in 30 days ($LD_{80/30}$), 100% of Camkk2 null animals and 20% of control animals survived for >30 days (FIG. 4B, P<0.0001). Although a higher radiation dose (900 cGy, $LD_{100/15}$. FIG. 10A) killed all control animals, approximately 40% of Camkk2 null animals survived for >30 days (FIG. 10, P<0.01).

Figure 4C:
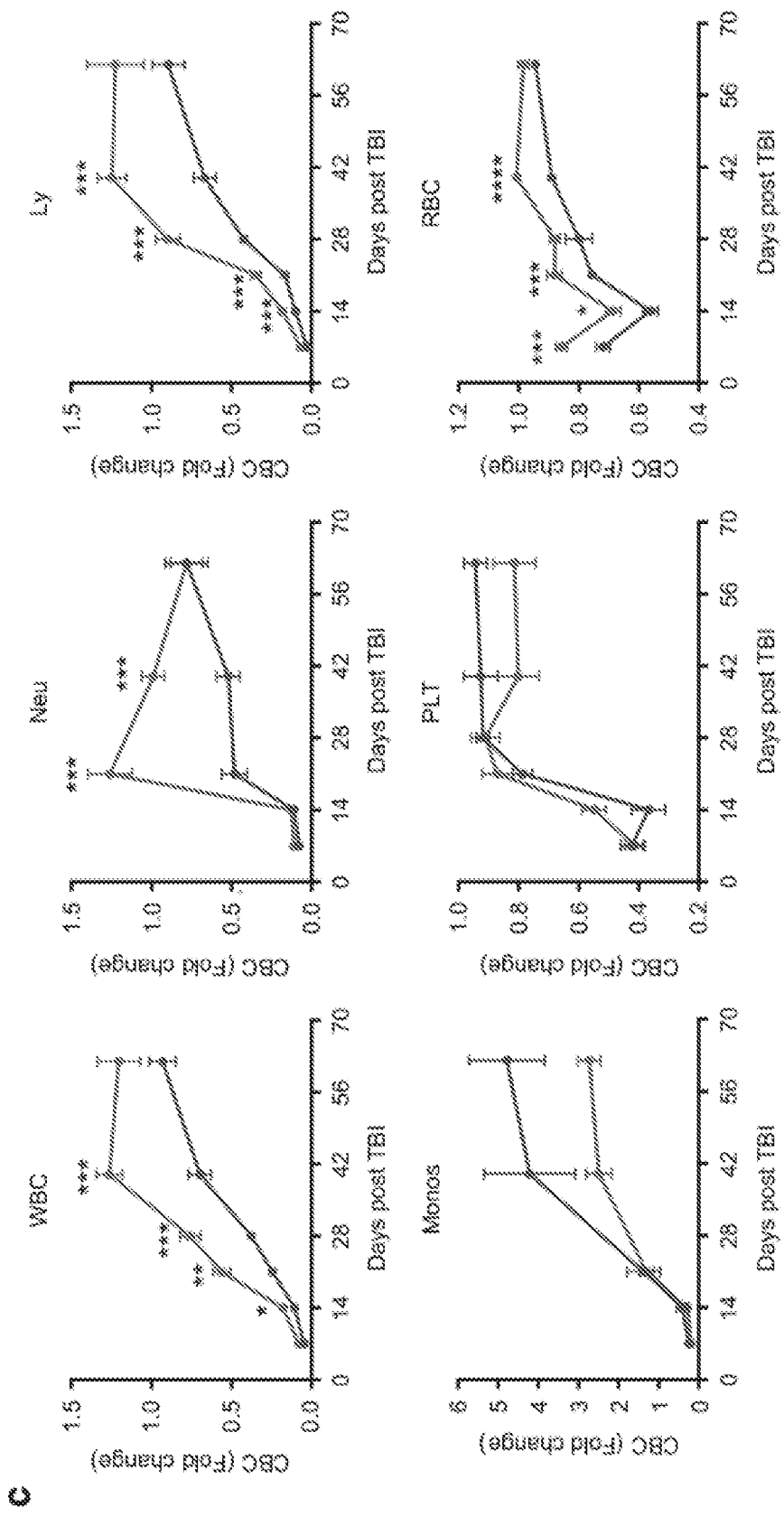
Figure 11A:
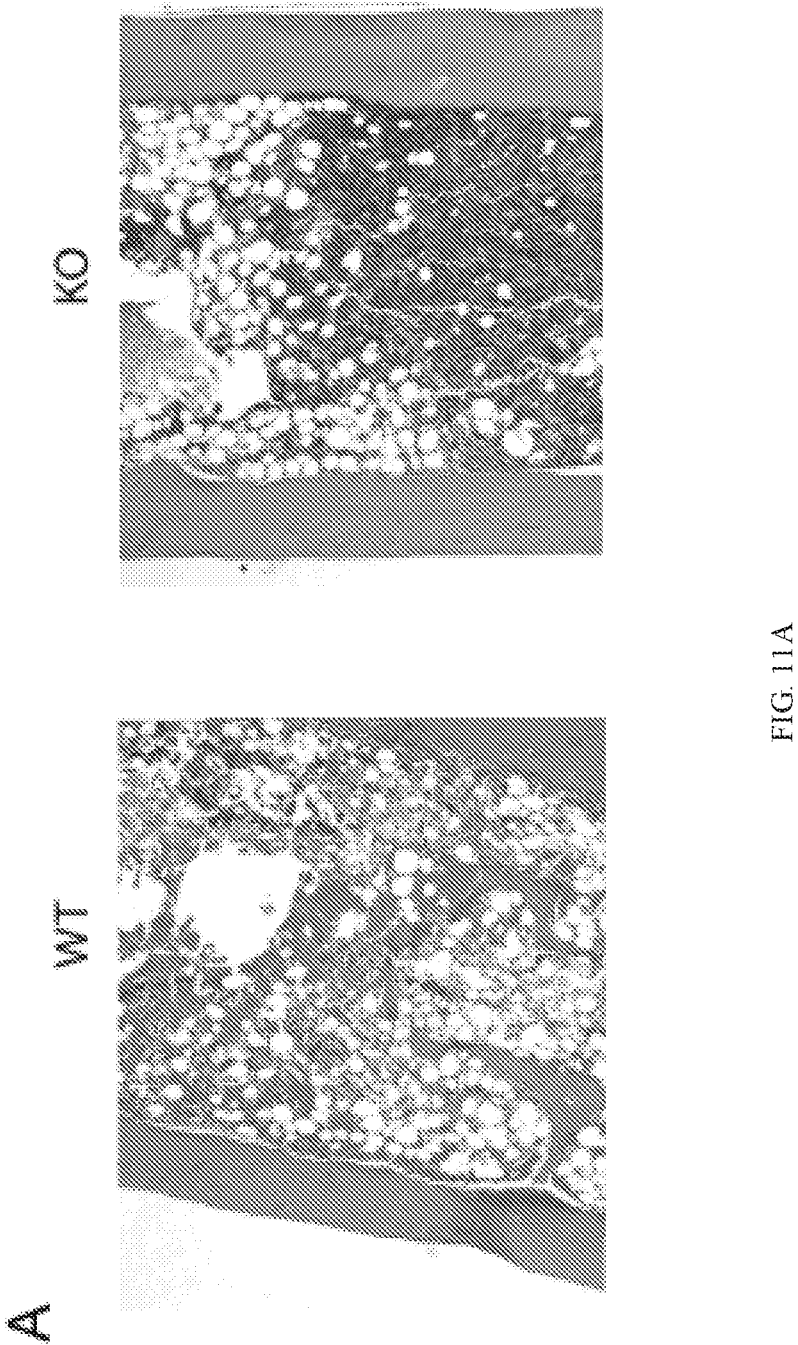
Figure 11B:
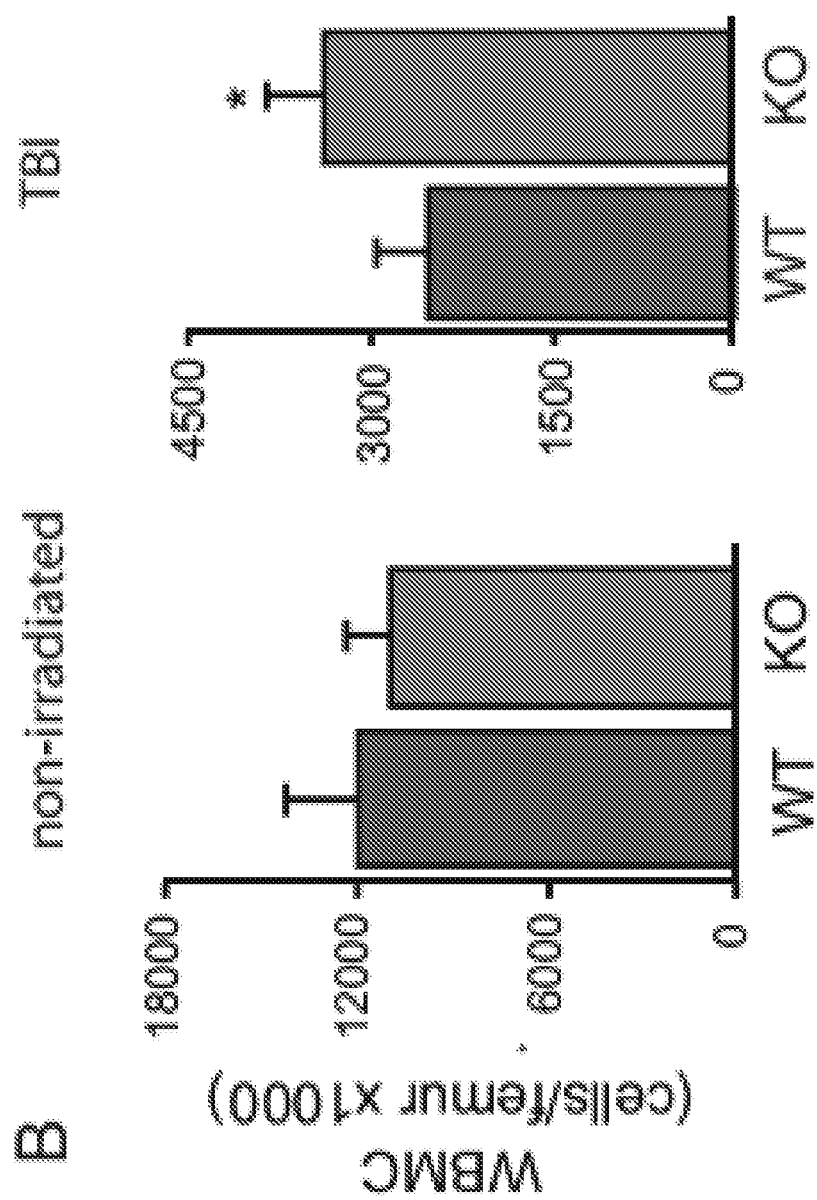
Figure 11C:
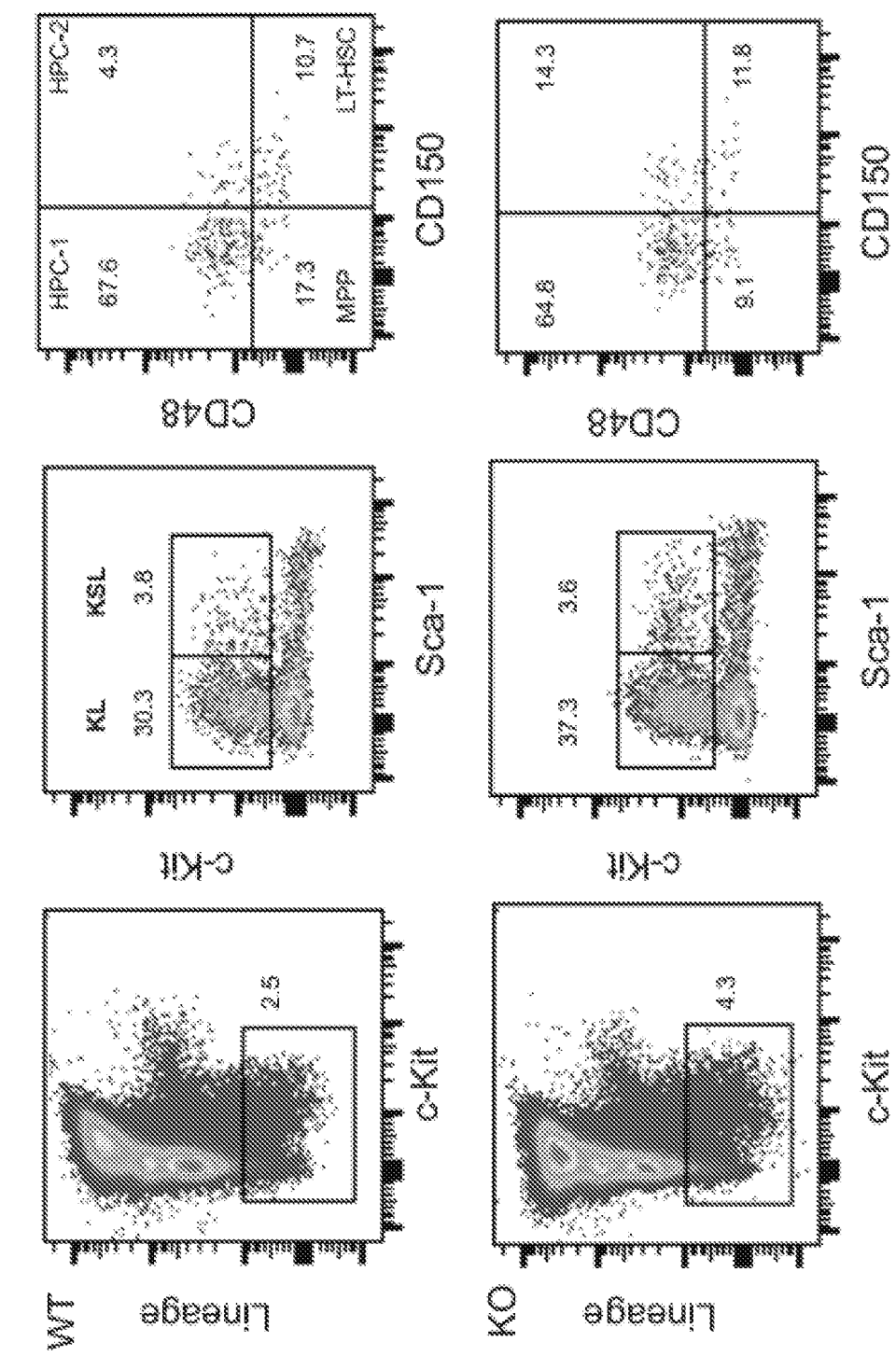

The peripheral blood cell count (CBC) recovery of irradiated mice was monitored using a single sublethal radiation dose (700 cGy). Non-irradiated Camkk2 null mice have significantly more monocytes and less white blood cells (WBCs), neutrophils, and lymphocytes in blood compared with WT mice. The number of red blood cells (RBCs) and platelets were comparable in WT and Camkk2 null mice (FIG. 10). The irradiated Camkk2 null mice have a better ability to regenerate neutrophils, leukocytes and RBC compared with WT mice (FIGS. 10B, 11C). In addition, the number of monocytes was also significantly higher in TBI Camkk2 null mice compared with WT mice (FIG. 10B). However, when normalized for the basal level, WT and Camkk2 null mice showed a comparable ability to regenerate monocytes and platelets following TBI (FIG. 4C and FIG. 10C).

To examine the BM content during regeneration, 700 cGy TBI control and Camkk2 null animals were sacrificed on day 14 and isolated BM for histology and flow cytometry analyses. The histological analysis indicated Camkk2 null animals had qualitatively higher BM cellularity than control mice (FIG. 11A, left) and there were significantly more cells in the marrow of irradiated Camkk2 null animals compared with WT mice (FIG. 11B; P<0.05). There were comparable numbers of WBMC in non-irradiated WT and Camkk2 null mice (FIG. 11B).

Figure 4D:
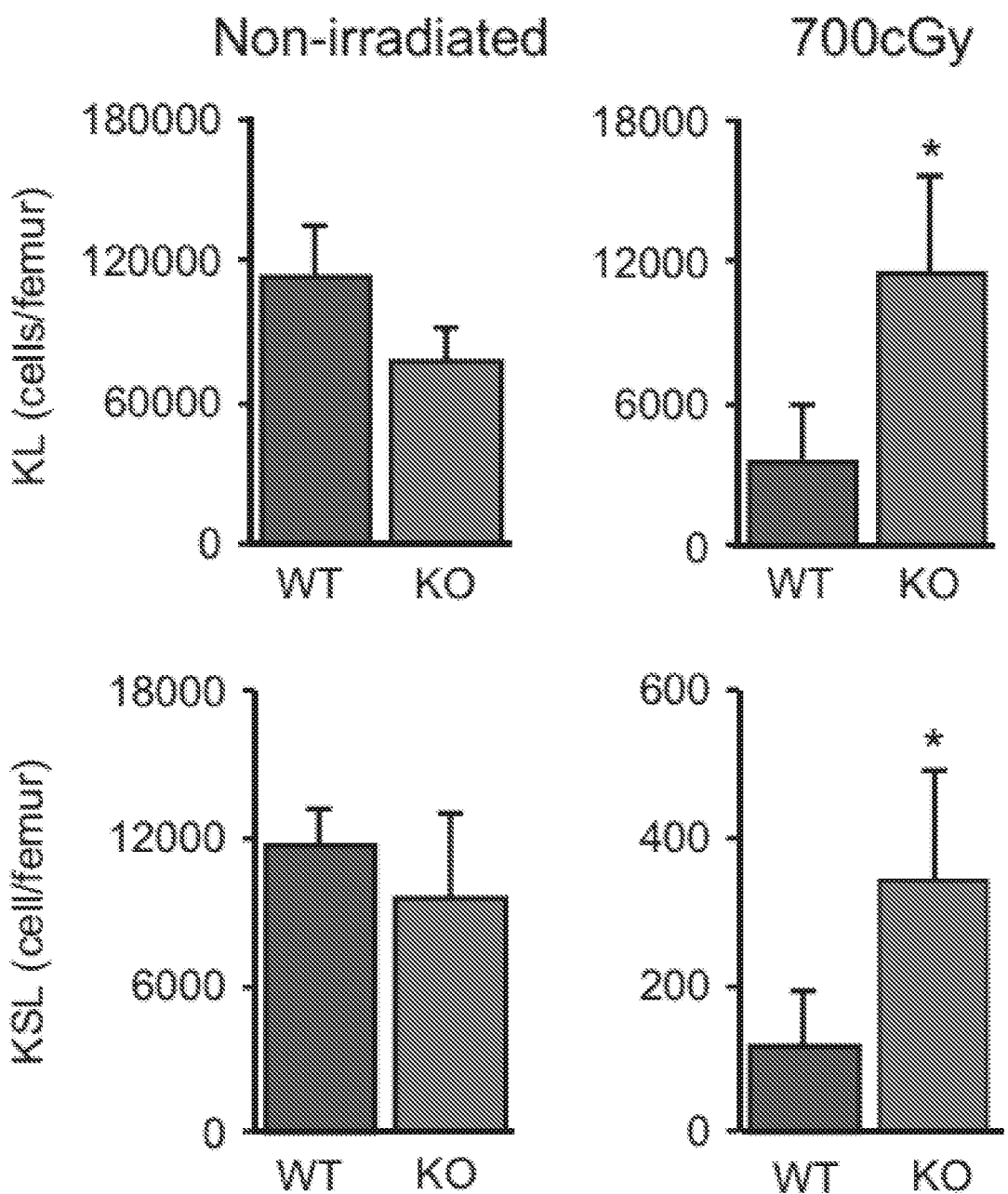
Figures 11D, 11E:
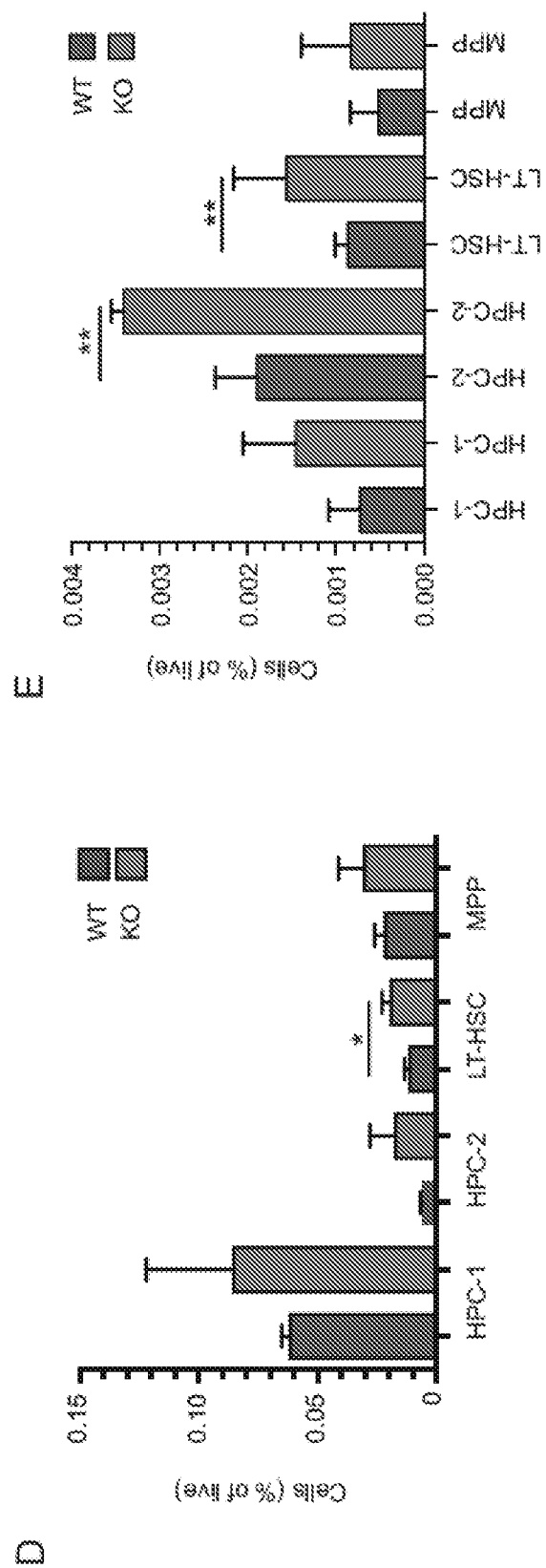

Whether the accelerated hematopoietic recovery was mediated by enhanced HSPC regeneration was assessed by analyzing the KL and KSL cell content in BM on day 14 following 700 cGy TBI. Although a trend of reduced absolute KL and KSL number in non-irradiated marrow was found, there were significantly more KL and KSL cells during hematopoietic regeneration (FIG. 4D). The SLAM KSL subsets were analyzed in TBI and non-irradiated mice based on the expression of CD48 and CD150 (FIG. 11C). The data show an increase in the percentage of LT-HSC in Camkk2 null mice under both homeostatic conditions and following TBI (FIG. 11D, left). In addition, the percentage of HPC-2 subsets was higher only in TBI Camkk2 null mice compared with control mice (FIG. 11D, right). Cumulatively, these data indicate Camkk2 null mice have accelerated HSPC recovery following radiation injury and this accounted for the faster hematopoietic recovery.

Example 6

Total Body Irradiated Camkk2 Null Mice have More Proliferating HSPC in BM

Figure 12A:
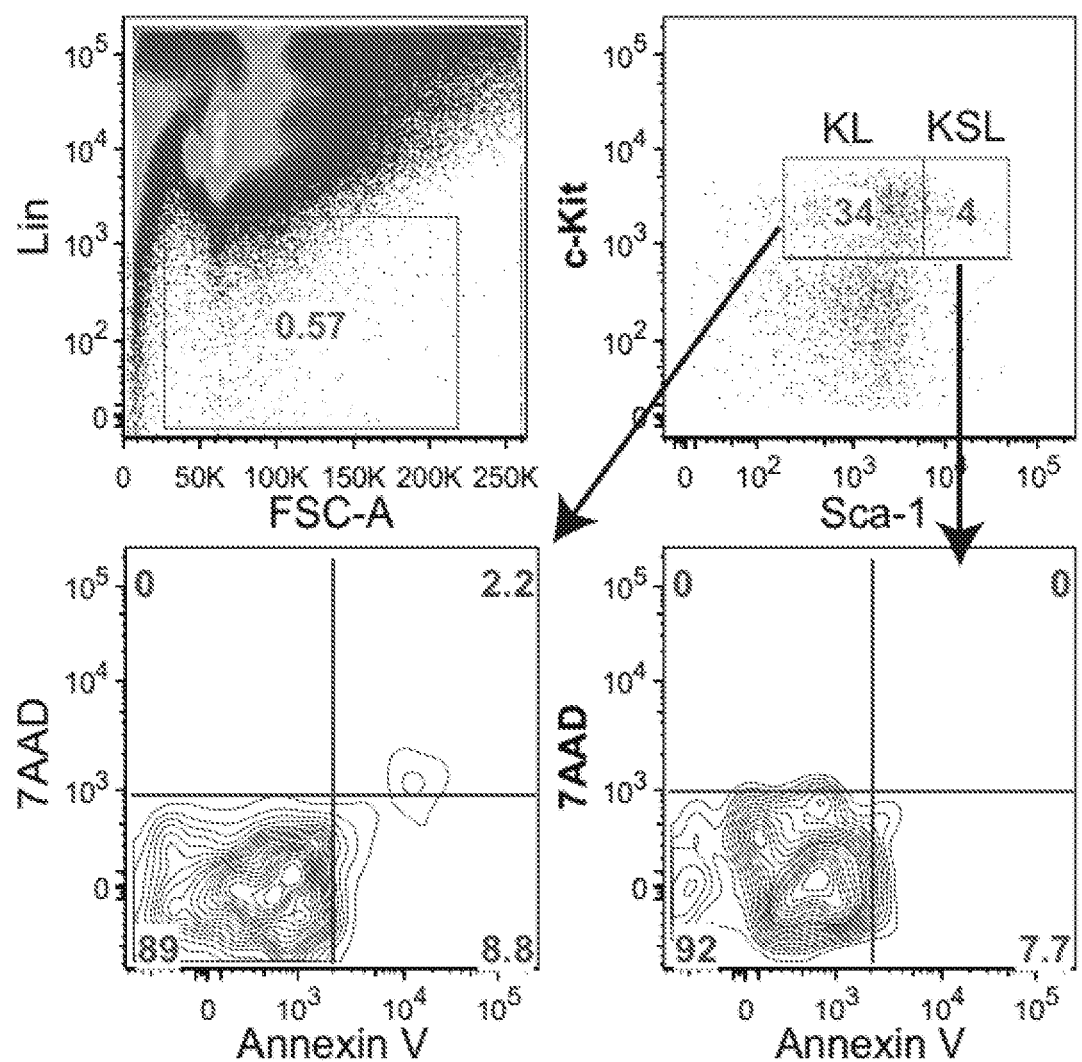
Figure 12B:
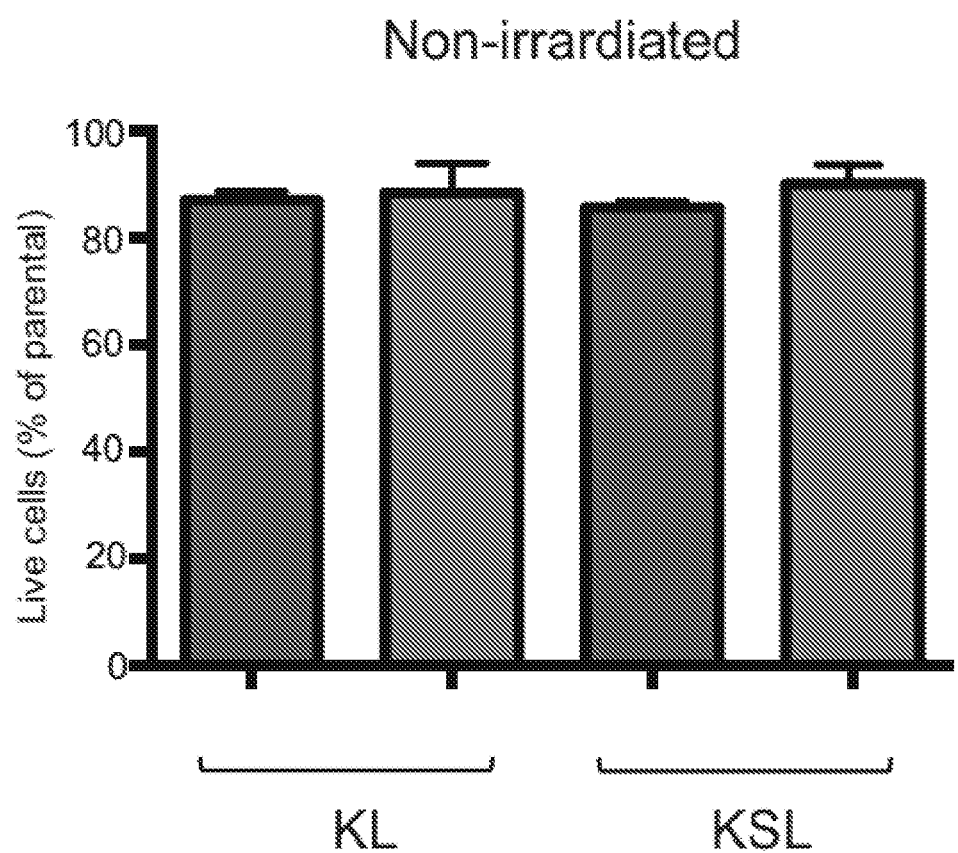
Figure 12C:
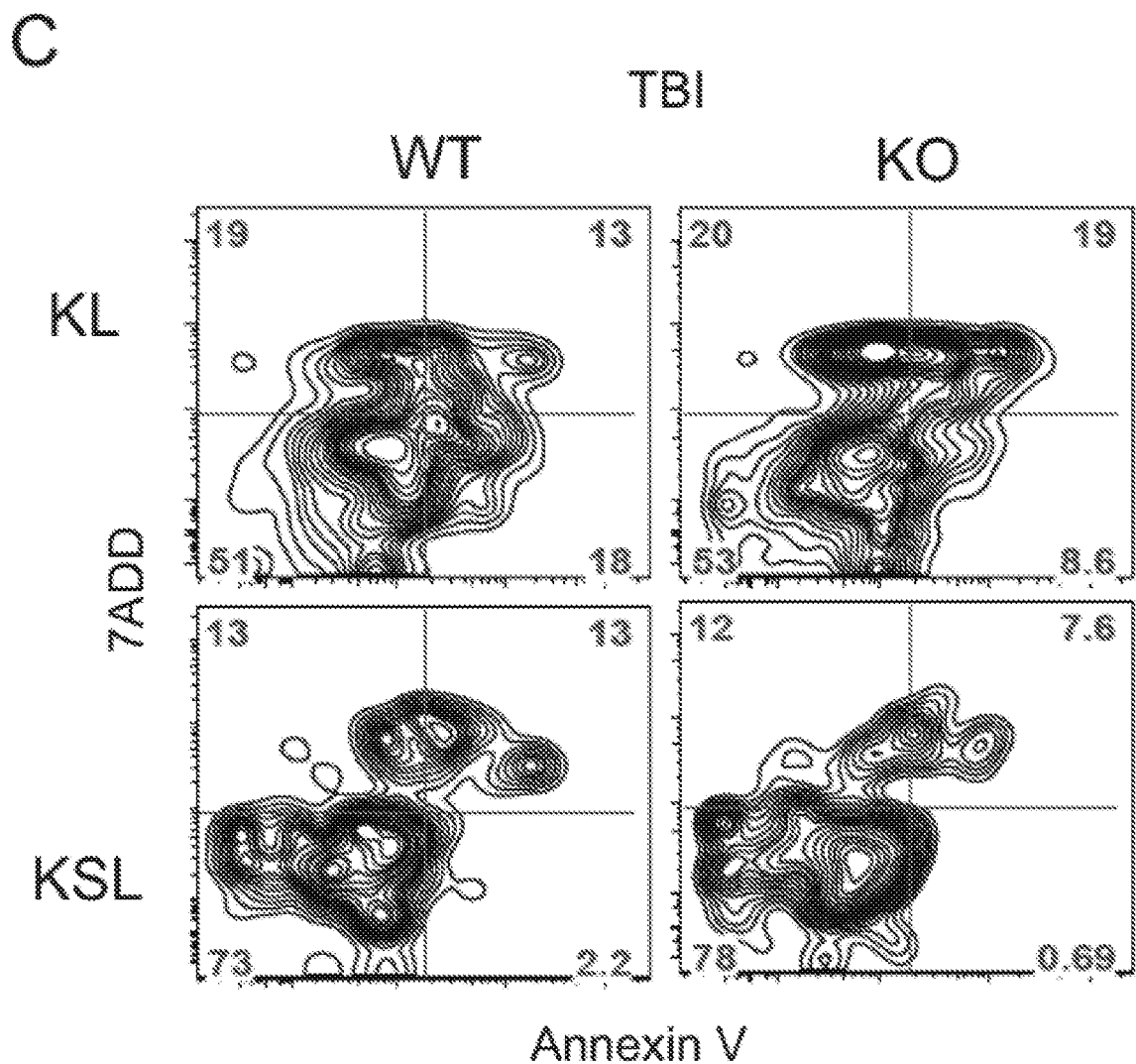
Figure 12D:
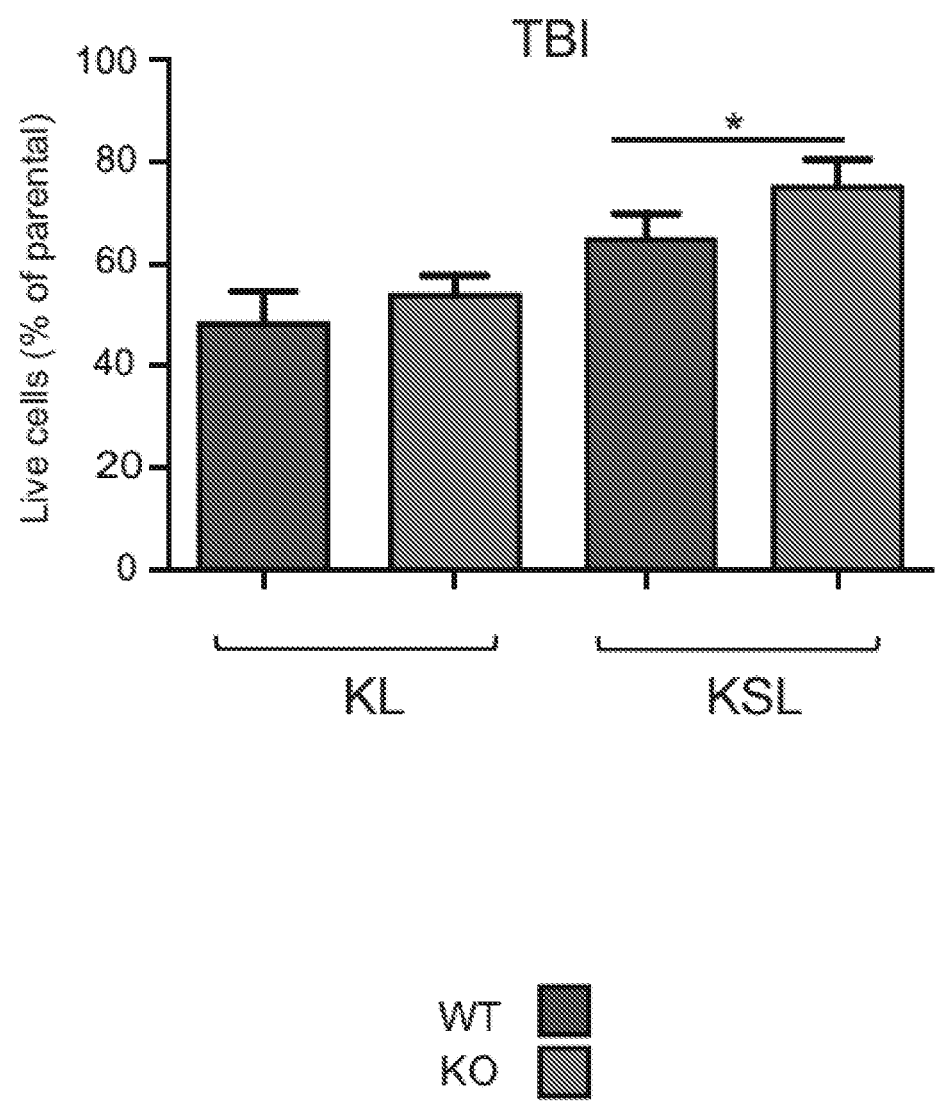

The in vivo sensitivity of HSPC to radiation-induced apoptosis was examined to determine the cellular basis of the accelerated hematopoietic recovery in Camkk2 null mice. Camkk2 deficiency does not impair the survival of HSPC in non-irradiated mice (FIGS. 12A, 12B). The data show a slight increase in live (10-15%) Camkk2 null KSL cells compared with WT KSL cells, but no differences in KL cells were observed 24 h after 450 cGy TBI (FIGS. 12C, 12D).

Figure 4E:
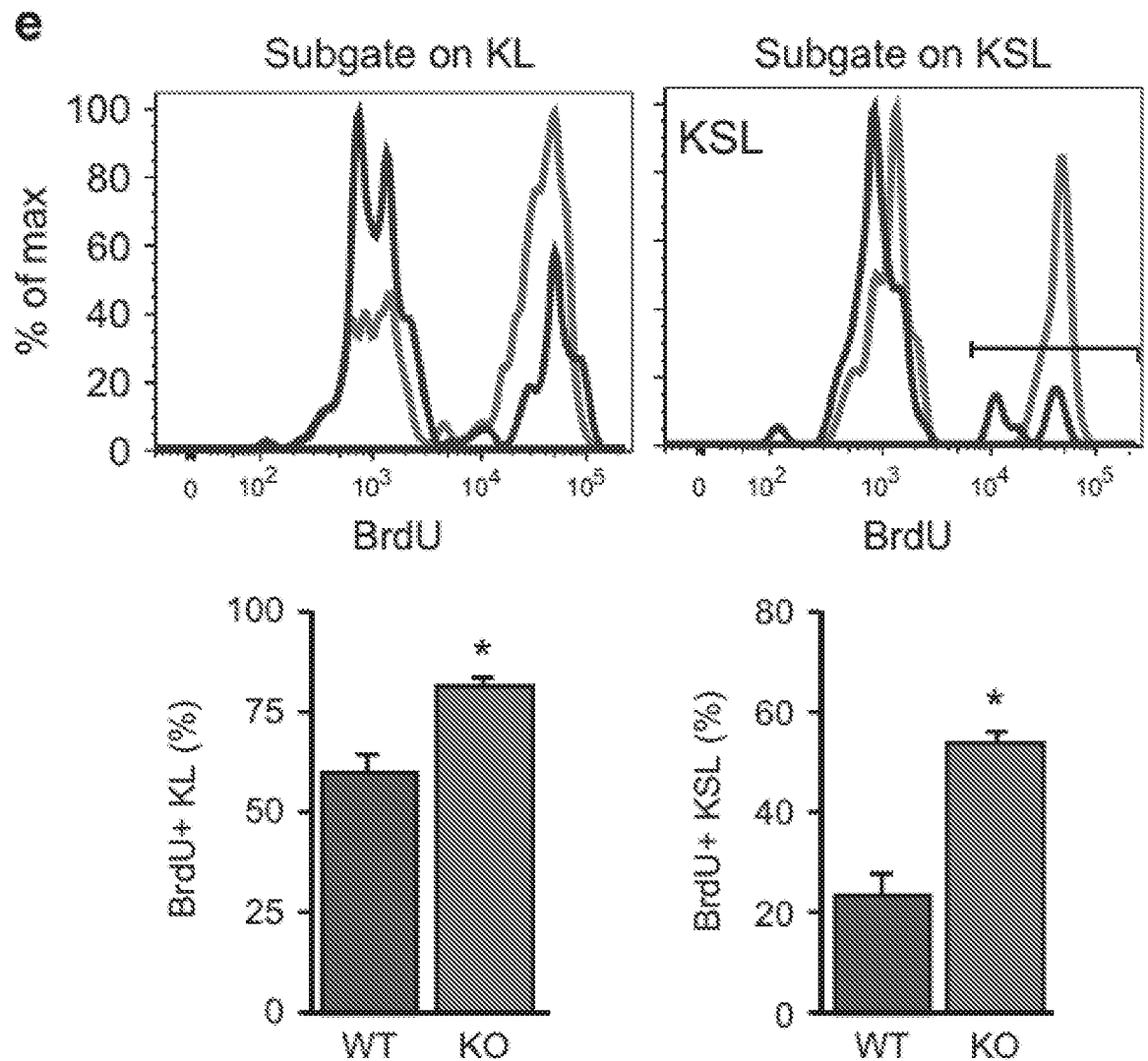

The proliferative response of the KL and KSL cells in the BM of regenerating control and Camkk2 null mice were examined on day 14 after 700 cGy TBI. Significantly more 5-bromo-2'-deoxyuridine (BrdU) incorporation was found in Camkk2 null KL and KSL cells during this period (FIG. 4E). The results indicate approximately 20% of control KSL cells are BrdU+, but >50% of Camkk2 null KSL cells are in cycle at day 14. To test whether the functional capacity of regenerated stem cells was decreased by the enhanced proliferation, competitive transplantation assays were performed using control and Camkk2 null KSL CD34⁻ cells harvested from the BM of 200 cGy TBI mice. Radiation did not induce differential HSC exhaustion or cause significant lineage skewing in the peripheral blood of recipient mice (FIG. 13). Cumulatively, these data demonstrate the loss of Camkk2 enhanced the proliferation of regenerating HSPC, which accelerates hematopoietic recovery.

Example 7

Camkk2 Null HSPC have a Cell-Intrinsic Enhanced Regenerative Capability In Vivo

To establish the cell-autonomous function of CaMMK2 on the regenerative capability of HSPC in vivo, KSL CD34⁻ cells were isolated from WT and Camkk2 null mice (CD45.2⁺) and transplanted the cells into lethally irradiated B6.SJL recipient mice (CD45.1⁺) with host competitor BM cells (FIG. 5A). The recipient mice were then monitored by CBC and CD45.2 chimerism was assessed. After 4 months, the transplanted mice showing comparable levels of CD45.2 chimerism were selected, irradiated with 450 cGy TBI, and then monitored for CD45.2 chimerism (FIG. 5A, B). During the regenerative phase, the CD45.2 chimerism in mice transplanted with WT KSL remained at levels comparable to pre-TBI. In contrast, a significant increase in CD45.2 chimerism was observed in mice transplanted with Camkk2 null HSC (FIG. 5C, FIG. 14). These findings provide direct evidence for a cell-intrinsic function of Camkk2 in regenerating HSPC because Camkk2 was ablated only in the transplanted KSL CD34– cells.

Example 8

CaMKK2 Couples Radiation Signaling with AMPK Anti-Proliferative Pathways

Figure 6A:
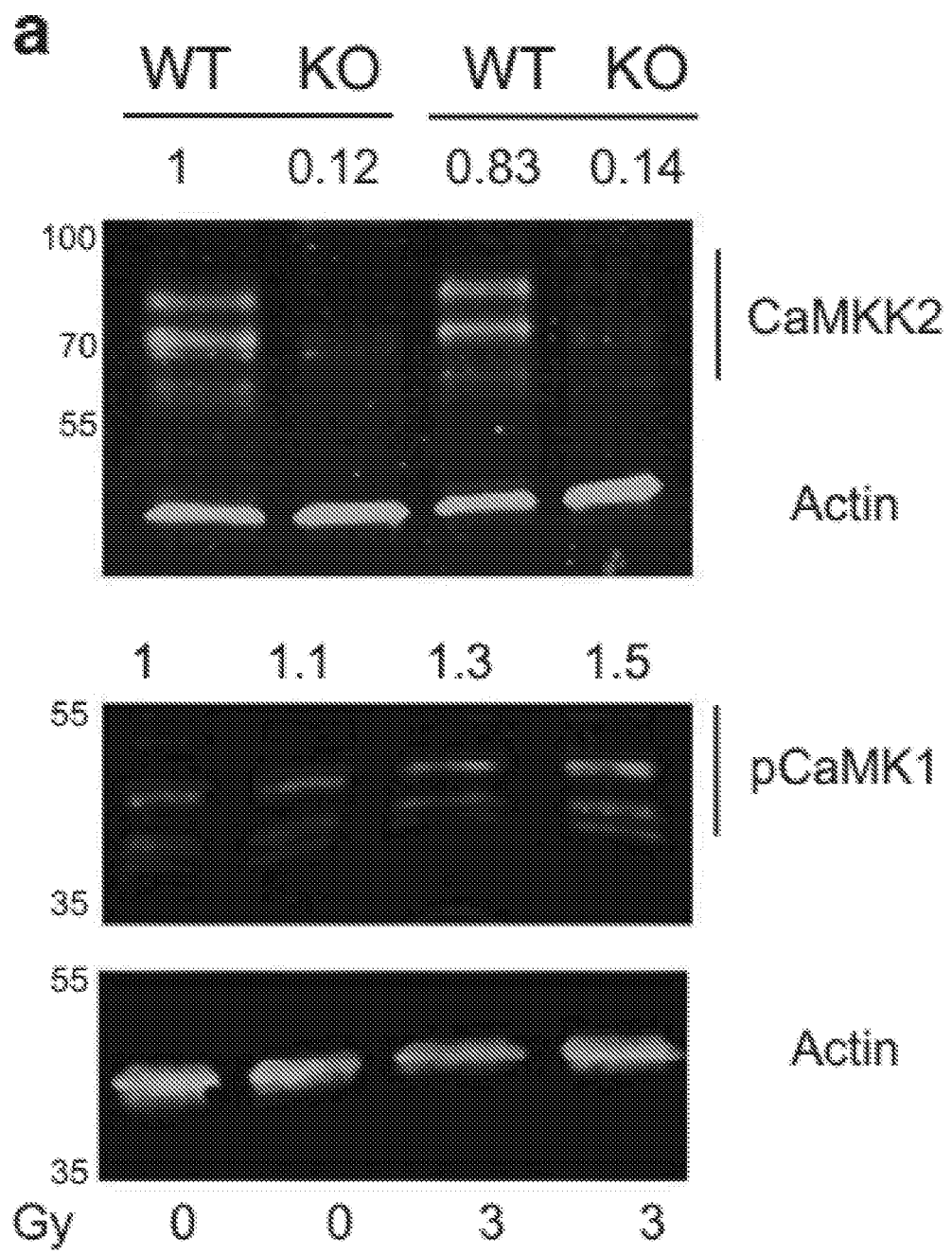
Figure 6B:
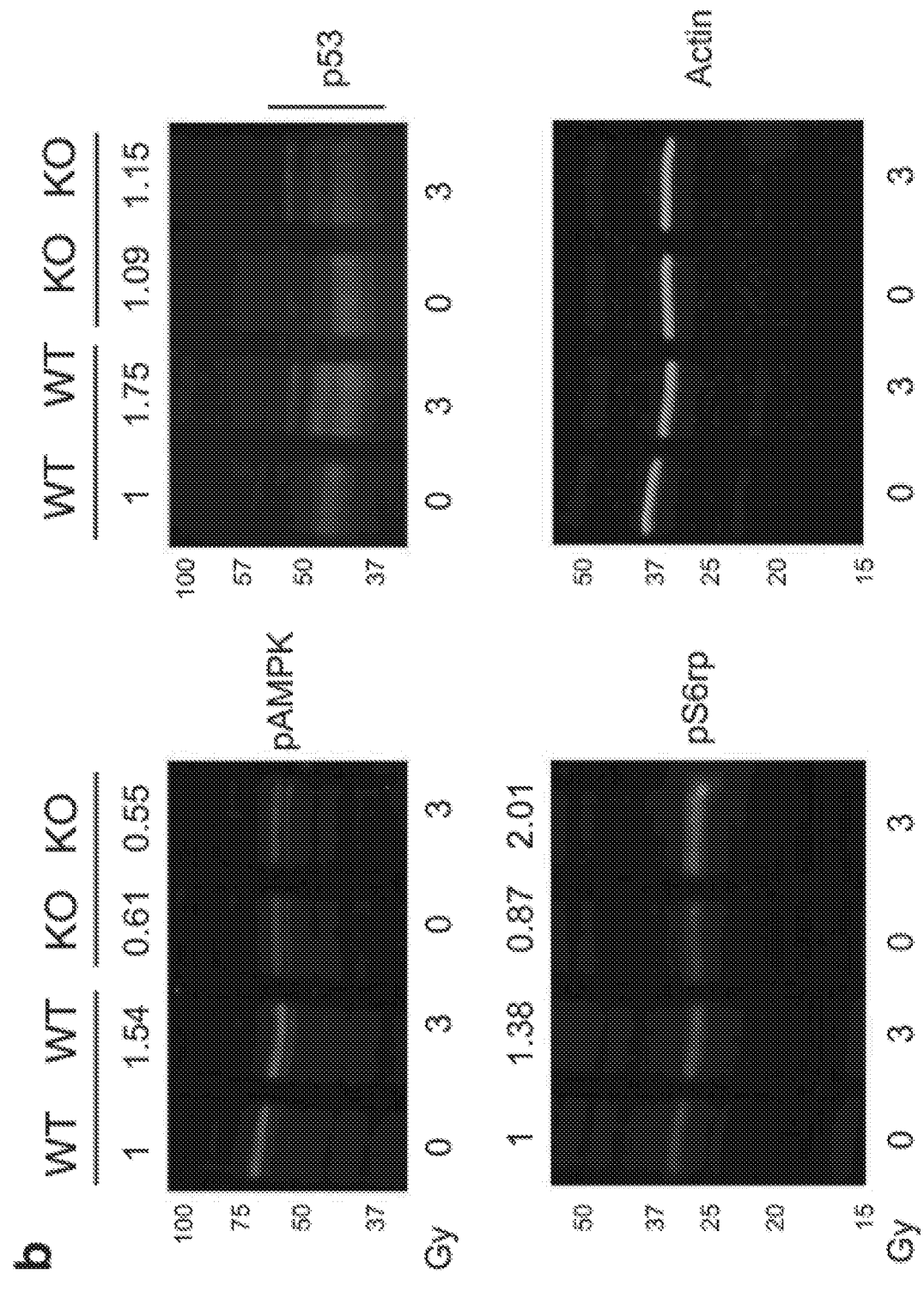

To investigate CaMKK2 function in radiation-induced signaling, lin⁻cKit⁺ cells (HSPC) were sorted from the BM of control and Camkk2 null mice and irradiated in vitro. The HSPC were then incubated for 60 min in culture medium and CaMKK2 and its known targets were evaluated in total cell lysates by immunoblotting. As expected, null mice lacked any detectable CaMKK2 protein in sorted HSPC (FIG. 6A). CaMKK2 loss did not impair the level of phospho-CaMKI in non-irradiated or irradiated HSPC (FIG. 6A). There was no CaMKIV or phospho-CaMKIV detected in homeostatic or irradiated cells (data not shown). Interestingly, Camkk2 null non-irradiated HSPC had significantly less phospho-AMPK and failed to induce phospho-AMPK after radiation (FIG. 6B). These results identify AMPK as the primary canonical target of CaMKK2 in HSPC and demonstrate CaMKK2 is required for coupling early radiation-induced signaling with AMPK activation.

AMPK is an evolutionarily conserved energy sensor that has an important role in cell proliferation, growth and survival. AMPK is also an important negative regulator of the Raptor-TSC-mTOR-S6K1 signaling pathway that controls S6 ribosomal protein (S6rp) to positively regulate cell proliferation. The level of phospho-S6rp in non-irradiated and irradiated HSPC was measured. Comparable levels of phospho-S6rp in non-irradiated WT and Camkk2 null HSPC were found. In contrast, more phospho-S6rp was detected in irradiated Camkk2 null HSPC compared with WT HSPC (1.3-versus 2.3-fold change, respectively; FIG. 6B).

The p53 protein is an important effector of radiation signaling and its role in the control of apoptosis, quiescence and proliferation of HSPC is well documented. Moreover, AMPK is a relevant upstream activator of the p53 pathway. Therefore, it was hypothesized that the CaMKK2-AMPK axis is involved in radiation signaling and regulates p53 stabilization. p53 was measured in WT and Camkk2 null HSPC irradiated in vitro with 300 cGy or left non-irradiated. The non-irradiated HSC from WT and Camkk2 null mice expressed comparable low levels of p53 (FIG. 6B). However, WT HSPC accumulated more p53 compared with Camkk2 null HSPC in response to radiation (FIG. 6B).

Figure 6C:
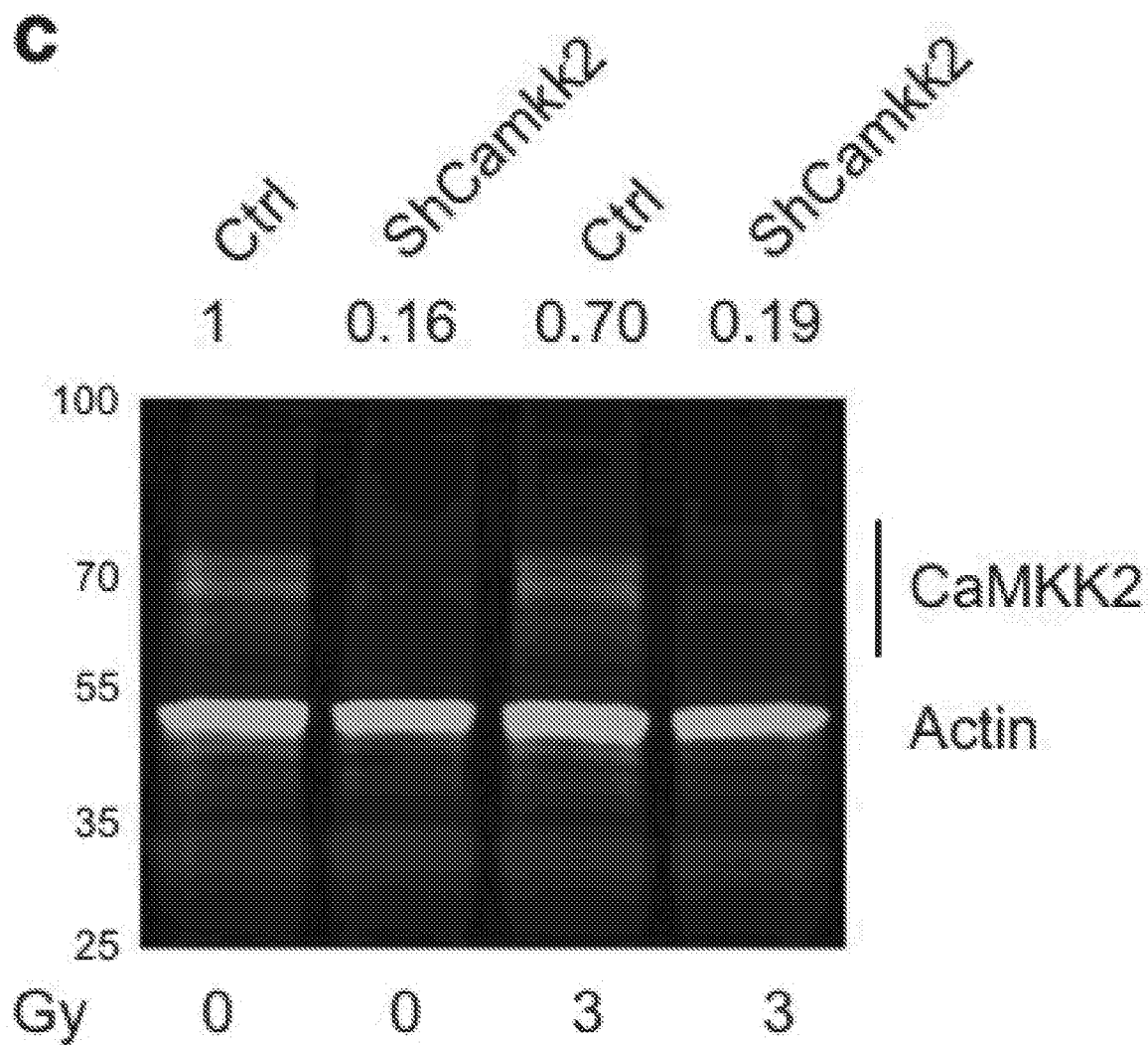
Figure 6D:
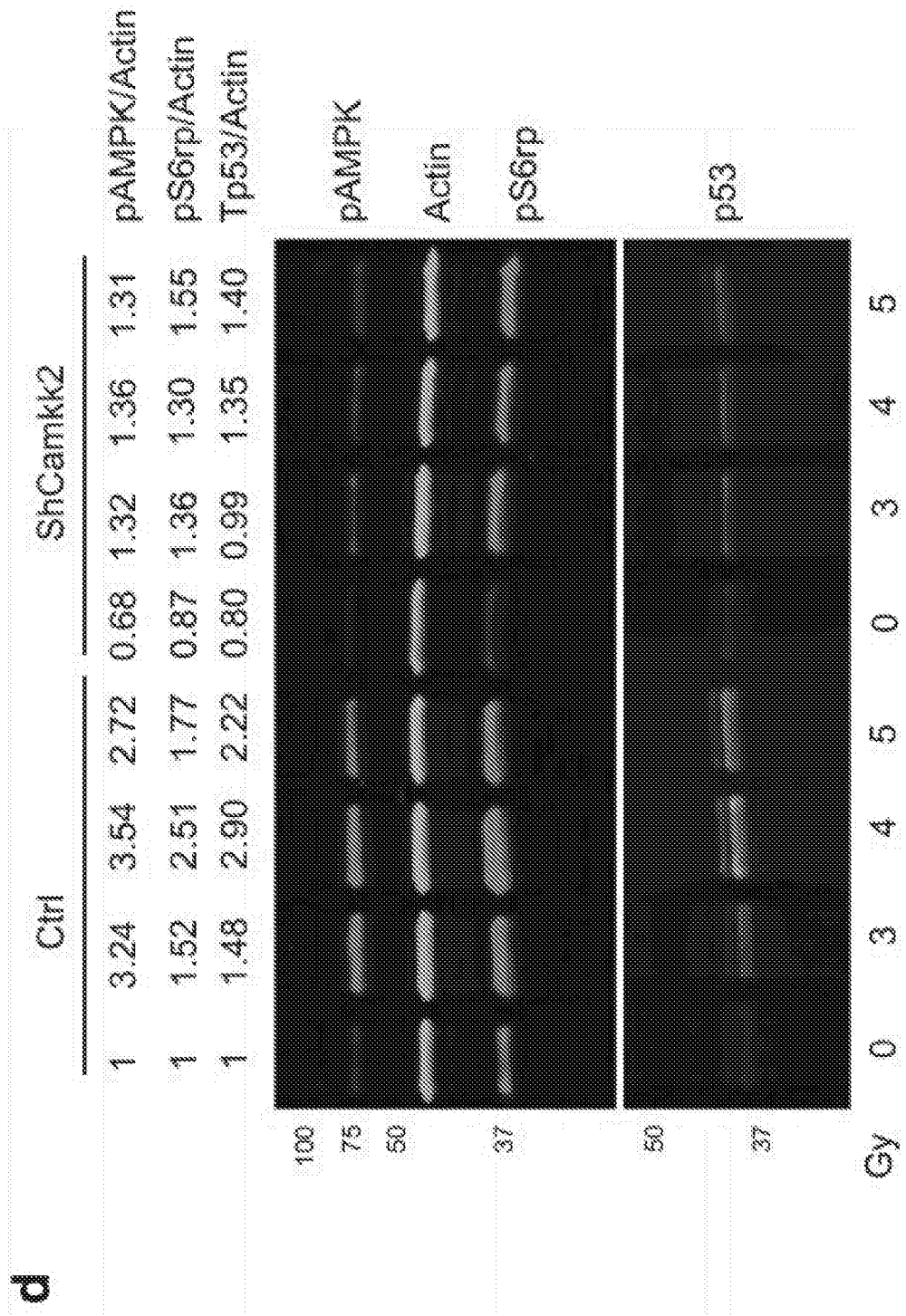

To further validate CaMKK2 function in radiation-induced signaling, lentiviral vectors were used to silence the expression of Camkk2 (ShCamkk2) in the M1 myeloid progenitor cell line (FIG. 6C). Camkk2 deficiency induced similar changes in the gene expression profile of KSL and M1 cells (FIGS. 15A, 15B). The levels of phospho-AMPK, phospho-S6rp and p53 were measured in control and ShCamkk2 M1 cells exposed to increasing radiation doses (300-500 cGy) or left non-irradiated (FIG. 6D). The radiation injury increased the phospho-AMPK and p53 levels in M1 control cells. In contrast, a minor increase in the phospho-AMPK and p53 levels was detected in ShCamkk2 M1 cells (FIG. 6D). Radiation increased phospho-S6rp levels in both control and ShCamkk2 M1 irradiated cells, which suggests M1 cells may have additional CaMKK2-independent signals that control phosphorylation of S6rp after radiation.

Figure 6E:
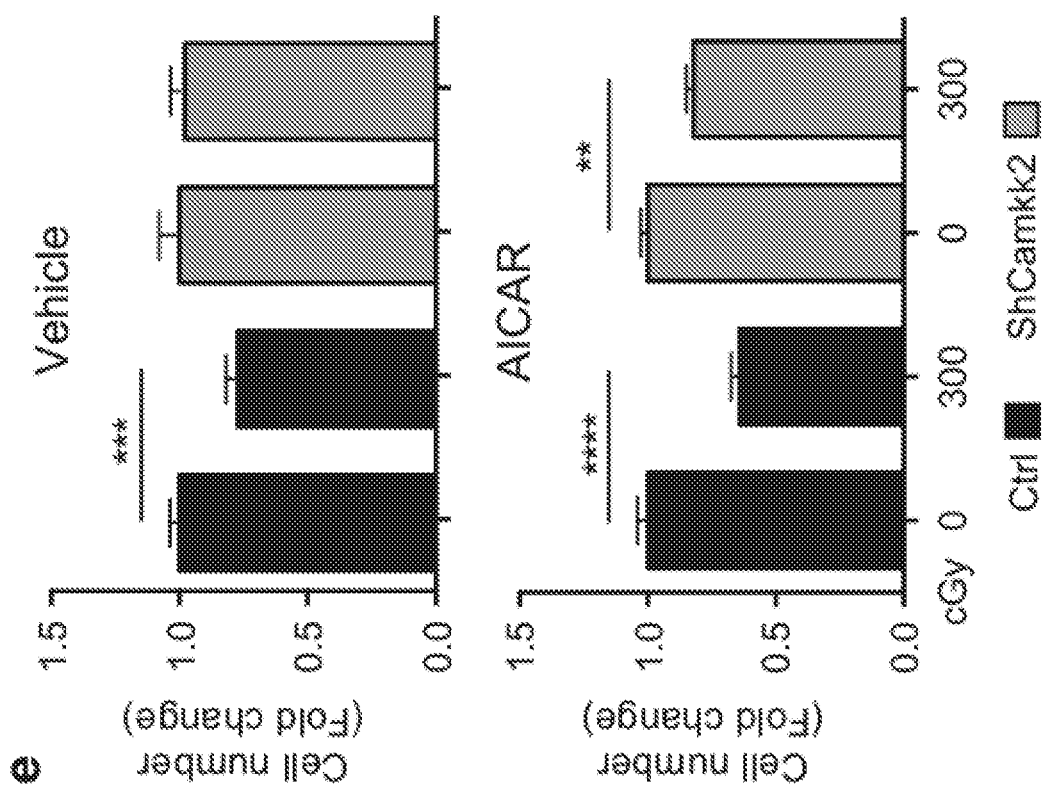

To determine the functional effects of Camkk2 deficiency in M1 cells, control and ShCamkk2 M1 cells were exposed to 300 cGy with or without a cell permeable AMPK agonist and the number of live M1 cells were determined 24 h after irradiation. Ionizing radiation decreased the proliferation of M1 control cells but did not affect ShCamkk2 M1 cells (FIG. 6E, top). The addition of the AMPK agonist 5-aminoimidazole-4-carboxamide 1-β-d-ribofuranoside, (AICAR), to the culture media reverted the refractory phenotype of ShCamkk2 M1 cells (FIG. 6E, bottom). There was no increase in cell death observed following radiation or AICAR treatment (data not shown). Collectively, these findings corroborate the hypothesis and demonstrate CaMKK2 is part of the signal pathway that activates AMPK/p53 signaling and mediates the anti-proliferative effect of radiation damage.

Example 9

Pharmacologic Inhibition of CaMKK2 Enhances Hematopoietic Regeneration In Vive

Figures 7A, 7B:
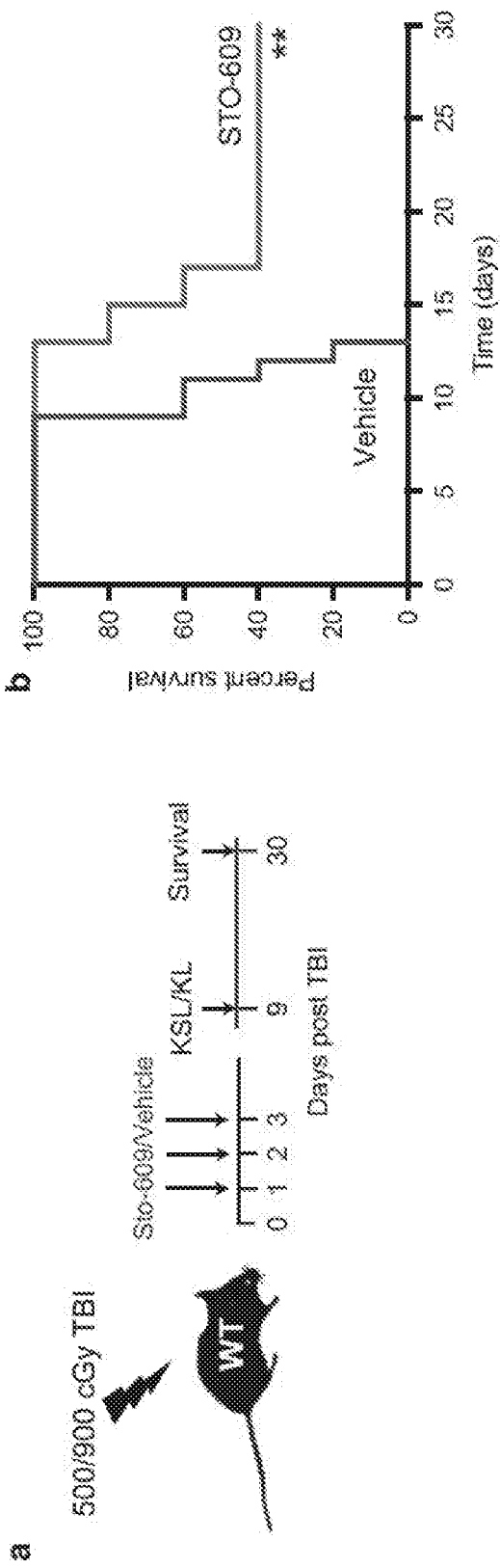
Figure 7C:
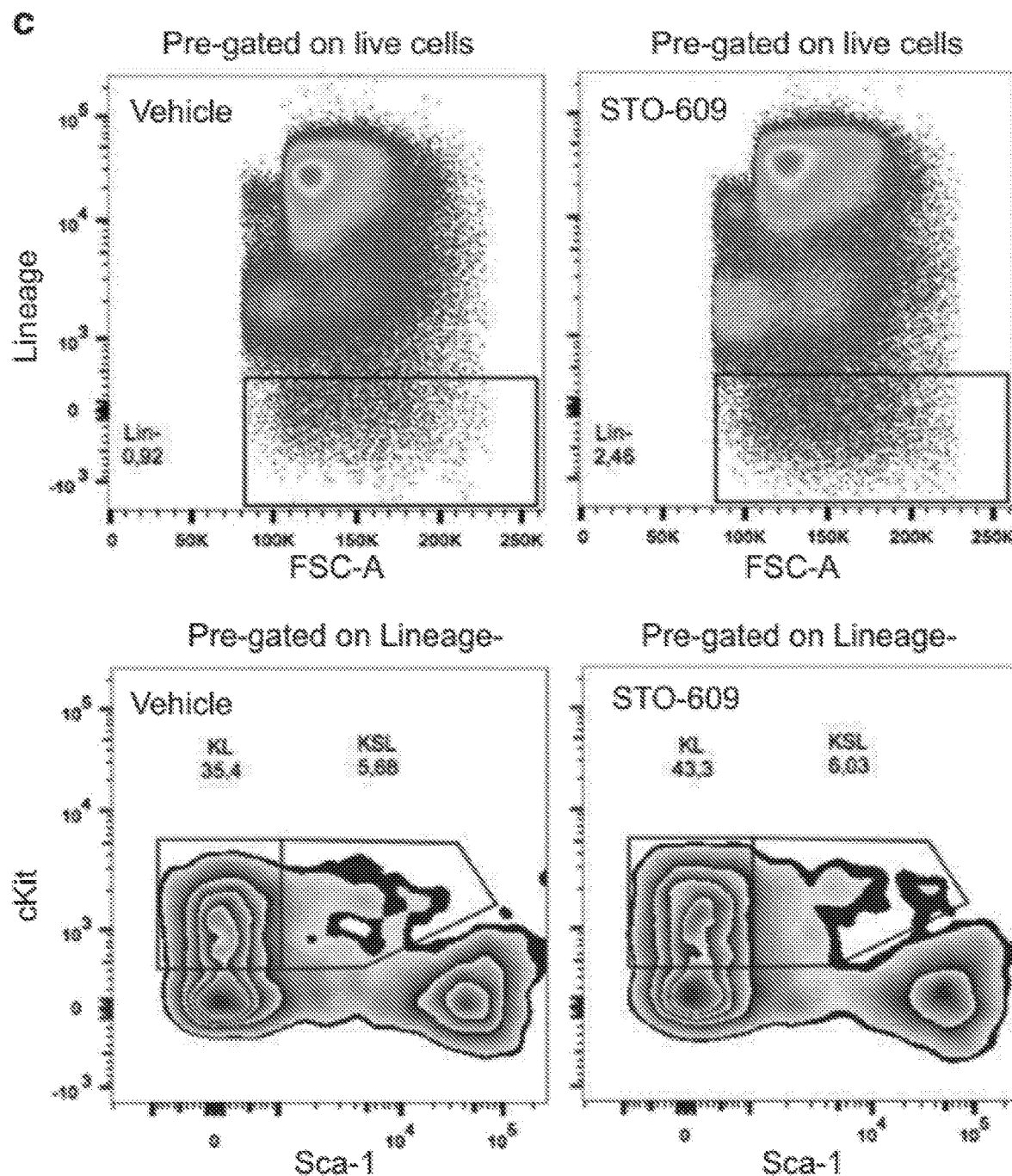
Figure 7D:
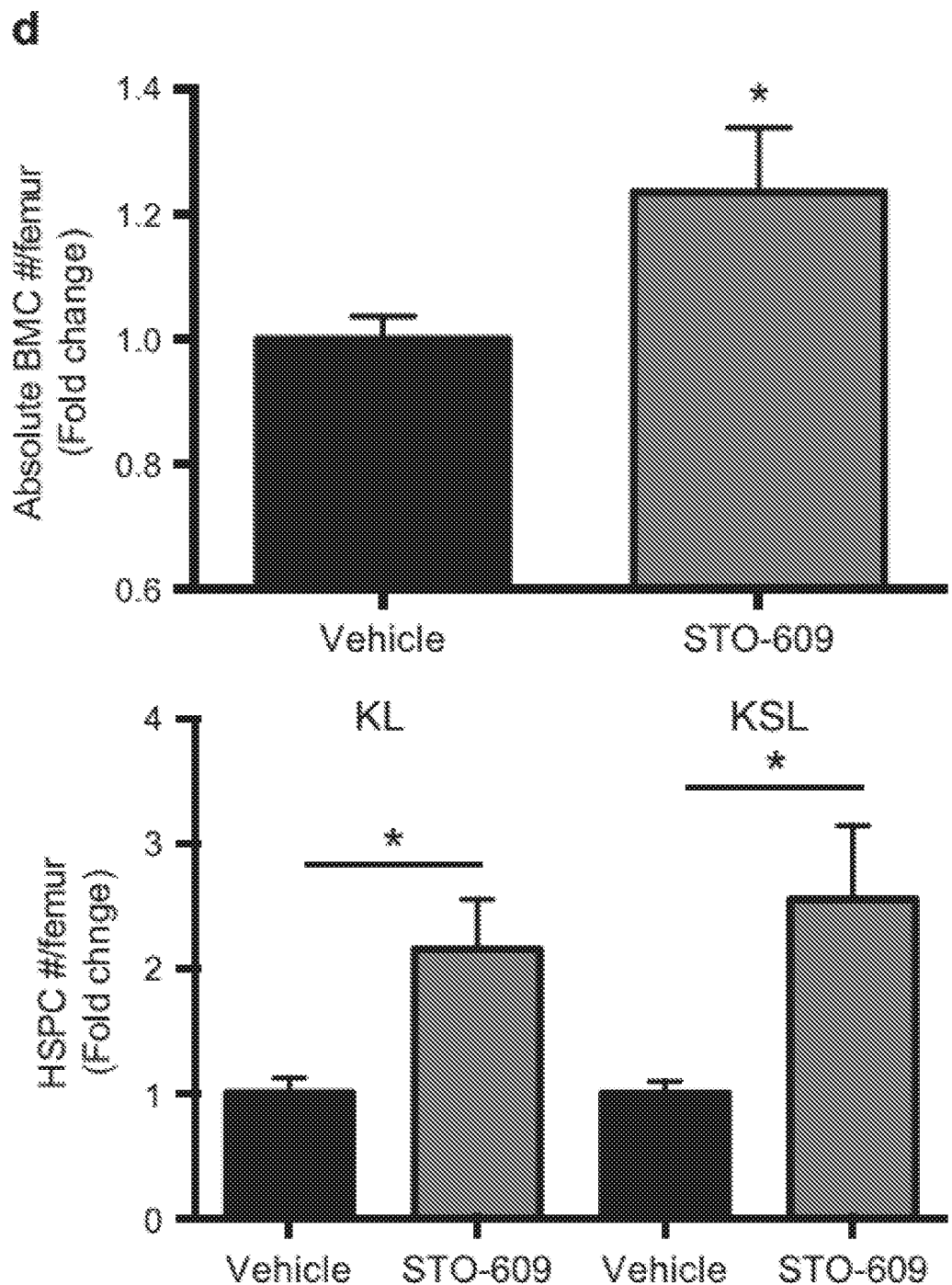

It was hypothesized that pharmacologic inhibition of CaMKK2 increases survival and HSPC recovery following TBI. To test this relevant translational implication of the findings set forth herein, a lethal radiation dose of 900 cGy TBI ($LD_{100/15}$) was delivered and then the animals were treated with either vehicle or the selective CaMKK2 inhibitor STO-609 (Tocris Biosciences). The administration of STO-609 at a dose of 10 µM/kg on days 1, 2 and 3 post-TBI significantly prolonged survival in the $LD_{100/15}$ model (FIGS. 7A, 7B). Next, the effects of STO-609 treatment on HSPC of mice receiving 500 cGy TBI were evaluated. More total BM cells and HSPC in the BM of mice 9 days after TBI were found (FIGS. 7C, 7D). Collectively, these findings indicate the transient administration of STO-609 after BM injury improves survival and expands HSPC.

The results presented herein uncover an important role for CaMKK2 in the mechanism controlling HSPC regeneration. CaMKK2 controls transcriptomic programs associated with stem cell quiescence and its loss stimulates HSPC regeneration in vivo. Interestingly, pharmacological inhibition of Camkk2 improves survival and accelerates HSPC recovery following hematopoietic radiation injury.

Example 10

Discussion

The interrelated processes of quiescence, proliferation and differentiation are tightly regulated in stem cells and this balance controls tissue regeneration after severe injuries. Extrinsic and HSC autonomous factors are involved in the fine tuning of these processes and defects in these molecular machineries are associated with high proliferative phenotype, significant decreases of HSC and progressive exhaustion of the hematopoietic compartment that culminates in premature death. Herein, it is shown that Camkk2 deletion in HSPC significantly downregulates genes affiliated with the quiescent stem cell signature. However, under homeostatic conditions Camkk2 null mice have only a slight decrease in HSPC number associated with mild alterations in blood cell counts. Camkk2 null mice do not develop a progressive exhaustion of the hematopoietic compartment or blood cancer with age (LR personal communication). These findings indicate Camkk2 loss does not affect HSPC under homeostatic conditions. On the contrary, Camkk2 null HSPC have a hyper-proliferative phenotype in vitro and an enhanced regenerative capability following BM damage. Interestingly, in conditions that mimic the functional cross talk in the niche, Camkk2 null KSL show higher functionality than WT cells. Collectively, these findings suggest CaMKK2 has a novel function in the signaling network involved in quiescence and the regenerative response of HSC in the niche.

Figure 6F:
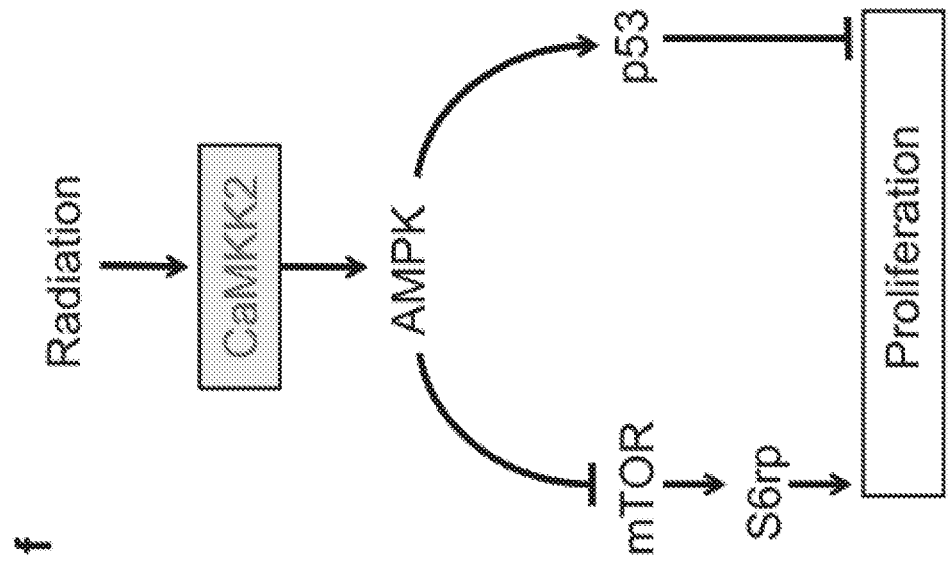

Herein, it is demonstrated that CaMKK2 links proximal radiation signaling to activation of the anti-proliferative AMPK/p53 signaling pathways (FIG. 6F). Under homeostatic conditions, CaMKK2 loss decreases phospho-T172

AMPK levels. This result suggests other upstream kinases such as Lkb1 contribute to AMPK regulation in quiescent HSC. The CaMKK2-AMPK axis is dispensable for maintaining homeostatic HSC, which is supported by the findings that germ-line deletion of Camkk2 or deletion of Ampk in the hematopoietic compartment does not impair hematopoiesis. Conversely, Lkb1 deletion is associated with a transient hyper-proliferative HSC response that is followed by an AMPK/mTOR independent catastrophic HSC depletion, pancytopenia and animal death. Ionizing radiation regulates AMPK activation in endothelial cells, mouse embryonic fibroblasts (MEFs) and cancer cells. However, the effect of radiation on AMPK in HSPC is poorly understood and the predominant upstream kinase responsible for radiation-induced AMPK activation is unknown. The results herein show CamKK2 may be the critical upstream kinase, and radiation activates AMPK in HSPC via CaMKK2. Camkk2 deletion prevents the inhibitory effects exerted by acute activation of AMPK on downstream effectors of mTOR signaling and p53, which control HSC proliferation under stress. The protein p53 is an important effector of the anti-proliferative effects of radiation and studies have shown short-term p53 inhibition following radiation damage facilitates hematopoietic recovery and prevents development of radiation-induced lymphomas. Importantly, p53 is a target of AMPK kinase. Herein it is demonstrated for the first time that CaMKK2 is required for p53 accumulation following radiation injury.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, compositions, or methods of use of the invention, may be made without departing from the spirit and scope thereof.

For reasons of completeness, various aspects of the invention are set out in the following numbered clauses:

Clause 1: A method of promoting regeneration of hematopoietic stem and progenitor cells (HSPCs) in a subject in need thereof, the method comprising administering to the subject an effective amount of a composition comprising a CaMKK2 inhibitor.

Clause 2: The method of clause 1, wherein the composition is administered to the subject to promote regeneration of HSPCs following bone marrow injury in the subject.

Clause 3: The method of clause 2, wherein the bone marrow injury in the subject is a radiation injury.

Clause 4: The method of clause 3, wherein the radiation injury in the subject is caused by total body irradiation.

Clause 5: The method of any one of clauses 1-4, wherein the subject has or is at risk of developing acute hematopoietic radiation syndrome.

Clause 6: The method of any one of clauses 1-5, wherein the CaMKK2 inhibitor is 7H-benzimidazo(2,1-a)benz(de)isoquinoline-7-one-3-carboxylic acid (STO-609).

Clause 7: The method of any one of clauses 1-6, wherein the composition is administered to the subject in a dose of 1 mg/kg to 10 mg/kg.

Clause 8: The method of any one of clauses 1-7, wherein the composition is administered to the subject once a day over the course of 1, 2, 3, 4, or 5 days following bone marrow injury.

Clause 9: The method of clause 8, wherein the composition is administered to the subject once a day over the course of 3 days following bone marrow injury.

Clause 10: The method of any one of clauses 1-9, wherein the subject is a mammal.

Clause 11: The method of any clause 10, wherein the subject is a human.

What is claimed is:

1. A method of promoting regeneration of hematopoietic stem and progenitor cells (HSPCs) in a subject in need thereof, the method comprising administering to the subject an effective amount of a composition comprising a CaMKK2 inhibitor; wherein the CaMKK2 inhibitor is 7H-benzimidazo(2,1-a)benz(de)isoquinoline-7-one-3 carboxylic acid (STO-609);
   wherein the composition is administered systemically to the subject in a dose of 1 mg/kg to 30 mg/kg;
   wherein the subject has a bone marrow injury; and,
   wherein the composition is administered to the subject for less than 5 days following the bone marrow injury in the subject.

2. The method of claim 1, wherein the bone marrow injury in the subject is a radiation injury.

3. The method of claim 2, wherein the radiation injury in the subject is caused by total body irradiation.

4. The method of claim 1, wherein the subject has or is at risk of developing acute hematopoietic radiation syndrome.

5. The method of claim 1, wherein the composition is administered to the subject once a day over the course of 1, 2, 3, or 4 days following bone marrow injury.

6. The method of claim 5, wherein the composition is administered to the subject once a day over the course of 3 days following bone marrow injury.

7. The method of claim 1, wherein the subject is a mammal.

8. The method of claim 7, wherein the subject is a human.

9. The method of claim 1, wherein the composition is administered to the subject orally or parenterally.

10. The method of claim 9, wherein parenteral administration comprises intraperitoneal administration.

* * * * *